(12) United States Patent
Bayer et al.

(10) Patent No.: US 8,872,906 B2
(45) Date of Patent: *Oct. 28, 2014

(54) ENDOSCOPE ASSEMBLY WITH A POLARIZING FILTER

(75) Inventors: Lex Bayer, Palo Alto, CA (US); Rupesh Desai, San Jose, CA (US); Alex Niel, Daly City, CA (US)

(73) Assignee: Avantis Medical Systems, Inc., Sunnyvale, CA (US)

( * ) Notice: Subject to any disclaimer, the term of this patent is extended or adjusted under 35 U.S.C. 154(b) by 1539 days.

This patent is subject to a terminal disclaimer.

(21) Appl. No.: 11/673,470

(22) Filed: Feb. 9, 2007

(65) Prior Publication Data

US 2007/0177009 A1    Aug. 2, 2007

Related U.S. Application Data

(63) Continuation-in-part of application No. 11/672,020, filed on Feb. 6, 2007, and a continuation-in-part of application No. 11/626,189, filed on Jan. 23, 2007, and a continuation-in-part of application No. 11/609,838, filed on Dec. 12, 2006, and a continuation-in-part of application No. 11/215,660, filed on Aug. 29, 2005, and a continuation-in-part of application No. 11/030,559, filed on Jan. 5, 2005, now abandoned.

(60) Provisional application No. 60/772,442, filed on Feb. 9, 2006.

(51) Int. Cl.
A62B 1/04      (2006.01)
A61B 1/00      (2006.01)
A61B 1/012     (2006.01)
A61B 1/05      (2006.01)

(52) U.S. Cl.
CPC ............... *A61B 1/05* (2013.01); *A61B 1/00177* (2013.01); *A61B 1/0125* (2013.01); *A61B 1/00096* (2013.01)
USPC ................................. 348/65; 348/45; 348/51

(58) Field of Classification Search
USPC ........................................... 348/65
See application file for complete search history.

(56) References Cited

U.S. PATENT DOCUMENTS 3,437,747 A    4/1969   Sheldon
3,610,231 A    10/1971  Takahashi et al.
(Continued)

FOREIGN PATENT DOCUMENTS

CN    1 628 603       6/2005
CN    1628603 A       6/2005
(Continued)

OTHER PUBLICATIONS

Invitation to Pay Additional Fees for PCT/US2007/002096, filed Jan. 23, 2007, mailed Jul. 6, 2007, 4 pgs.

(Continued)

*Primary Examiner* — Viet Vu
*Assistant Examiner* — Herman Belcher
(74) *Attorney, Agent, or Firm* — Morrison & Foerster LLP

(57) ABSTRACT

An endoscope includes an imaging device, a first polarizing filter disposed in front of the imaging device, a light source, and a second polarizing filter disposed in front of the light source. The planes of polarization of the first and second polarizing filters are at a substantially 90° angle.

14 Claims, 6 Drawing Sheets

(56) References Cited

U.S. PATENT DOCUMENTS

| | | | |
|---|---|---|---|
| 3,643,653 A | 2/1972 | Takahashi et al. | |
| 3,739,770 A | 6/1973 | Mori | |
| 3,889,662 A | 6/1975 | Mitsui | |
| 3,897,775 A | 8/1975 | Furihata | |
| 3,918,438 A | 11/1975 | Hayamizu et al. | |
| 4,261,344 A | 4/1981 | Moore et al. | |
| 4,351,587 A | 9/1982 | Matsuo et al. | |
| 4,398,811 A | 8/1983 | Nishioka et al. | |
| 4,494,549 A | 1/1985 | Namba et al. | |
| 4,573,450 A | 3/1986 | Arakawa | |
| 4,586,491 A | 5/1986 | Carpenter | |
| 4,602,281 A | 7/1986 | Nagasaki et al. | |
| 4,625,236 A | 11/1986 | Fujimori et al. | |
| 4,646,722 A | 3/1987 | Silverstein et al. | |
| 4,699,463 A | 10/1987 | D'Amelio et al. | |
| 4,721,097 A | 1/1988 | D'Amelio | |
| 4,727,859 A | 3/1988 | Lia | |
| 4,741,326 A | 5/1988 | Sidall et al. | |
| 4,742,817 A | 5/1988 | Kawashima et al. | |
| 4,790,295 A | 12/1988 | Tashiro | |
| 4,800,870 A | 1/1989 | Reid, Jr. | |
| 4,825,850 A | 5/1989 | Opie et al. | |
| 4,836,211 A | 6/1989 | Sekino et al. | |
| 4,846,154 A | 7/1989 | MacAnally et al. | |
| 4,852,551 A | 8/1989 | Opie et al. | |
| 4,853,773 A | 8/1989 | Hibino et al. | |
| 4,862,873 A | 9/1989 | Yajima et al. | |
| 4,867,138 A | 9/1989 | Kubota et al. | |
| 4,869,238 A | 9/1989 | Opie et al. | |
| 4,870,488 A | 9/1989 | Ikuno et al. | |
| 4,873,572 A | 10/1989 | Miyazaki et al. | |
| 4,873,965 A | 10/1989 | Danieli | |
| 4,884,133 A | 11/1989 | Kanno et al. | |
| 4,899,732 A | 2/1990 | Cohen | |
| 4,905,667 A | 3/1990 | Foerster et al. | |
| 4,907,395 A | 3/1990 | Opie et al. | |
| 4,911,148 A | 3/1990 | Sosnowski et al. | |
| 4,911,564 A | 3/1990 | Baker | |
| 4,926,258 A | 5/1990 | Sasaki | |
| 4,947,827 A | 8/1990 | Opie et al. | |
| 4,947,828 A | 8/1990 | Carpenter et al. | |
| 4,979,496 A | 12/1990 | Komi | |
| 4,991,565 A | 2/1991 | Takahashi et al. | |
| 5,019,040 A | 5/1991 | Itaoka et al. | |
| 5,025,778 A | 6/1991 | Silverstein et al. | |
| 5,026,377 A | 6/1991 | Burton et al. | |
| 5,050,585 A | 9/1991 | Takahashi | |
| RE34,110 E | 10/1992 | Opie et al. | |
| 5,159,446 A | 10/1992 | Hibino et al. | |
| 5,166,787 A | 11/1992 | Irion | |
| 5,178,130 A | 1/1993 | Kaiya et al. | |
| 5,187,572 A | 2/1993 | Nakamura et al. | |
| 5,193,525 A | 3/1993 | Silverstein et al. | |
| 5,196,928 A | 3/1993 | Karasawa et al. | |
| 5,253,638 A | 10/1993 | Tamburrino et al. | |
| 5,260,780 A | 11/1993 | Staudt, III | |
| 5,271,381 A | 12/1993 | Ailinger et al. | |
| 5,305,121 A | 4/1994 | Moll | |
| 5,318,031 A | 6/1994 | Mountford et al. | |
| 5,329,887 A | 7/1994 | Ailinger et al. | |
| 5,337,734 A | 8/1994 | Saab | |
| 5,381,784 A | 1/1995 | Adair | |
| 5,398,685 A | 3/1995 | Wilk et al. | |
| 5,406,938 A * | 4/1995 | Mersch et al. | 600/138 |
| 5,434,669 A | 7/1995 | Tabata et al. | |
| 5,443,781 A | 8/1995 | Saab | |
| 5,447,148 A | 9/1995 | Oneda et al. | |
| 5,483,951 A | 1/1996 | Frassica et al. | |
| 5,494,483 A | 2/1996 | Adair | |
| 5,518,501 A | 5/1996 | Oneda et al. | |
| 5,520,607 A | 5/1996 | Frassica et al. | |
| 5,530,238 A | 6/1996 | Meulenbrugge et al. | |
| 5,533,496 A | 7/1996 | De Faria-Correa et al. | |
| 5,536,236 A | 7/1996 | Yabe et al. | |
| 5,556,367 A | 9/1996 | Yabe et al. | |
| 5,613,936 A | 3/1997 | Czarnek et al. | |
| 5,614,943 A | 3/1997 | Nakamura et al. | |
| 5,626,553 A | 5/1997 | Frassica et al. | |
| 5,634,466 A | 6/1997 | Gruner | |
| 5,653,677 A | 8/1997 | Okada et al. | |
| 5,667,476 A | 9/1997 | Frassica et al. | |
| 5,679,216 A | 10/1997 | Takayama et al. | |
| 5,681,260 A | 10/1997 | Ueda et al. | |
| 5,682,199 A | 10/1997 | Lankford | |
| 5,685,822 A | 11/1997 | Harhen | |
| 5,692,729 A | 12/1997 | Harhen | |
| 5,696,850 A | 12/1997 | Parulski et al. | |
| 5,702,348 A | 12/1997 | Harhen | |
| 5,706,128 A | 1/1998 | Greenberg | |
| 5,711,299 A | 1/1998 | Manwaring et al. | |
| 5,722,933 A | 3/1998 | Yabe et al. | |
| 5,752,912 A | 5/1998 | Takahashi et al. | |
| 5,762,603 A | 6/1998 | Thompson | |
| 5,817,061 A | 10/1998 | Goodwin et al. | |
| 5,827,177 A | 10/1998 | Oneda et al. | |
| 5,833,603 A | 11/1998 | Kovacs et al. | |
| 5,843,103 A | 12/1998 | Wulfman | |
| 5,843,460 A | 12/1998 | Labigne et al. | |
| 5,854,859 A | 12/1998 | Sobol | |
| 5,860,914 A | 1/1999 | Chiba et al. | |
| 5,876,329 A | 3/1999 | Harhen | |
| 5,916,147 A | 6/1999 | Boury | |
| 5,924,977 A | 7/1999 | Yabe et al. | |
| 5,938,587 A | 8/1999 | Taylor et al. | |
| 5,982,932 A | 11/1999 | Prokoski | |
| 5,989,182 A | 11/1999 | Hori et al. | |
| 5,989,224 A | 11/1999 | Exline et al. | |
| 6,017,358 A | 1/2000 | Yoon | |
| 6,026,323 A | 2/2000 | Skladnev et al. | |
| 6,066,090 A | 5/2000 | Yoon | |
| 6,099,464 A | 8/2000 | Shimizu et al. | |
| 6,099,466 A | 8/2000 | Sano et al. | |
| 6,099,485 A | 8/2000 | Patterson | |
| 6,106,463 A | 8/2000 | Wilk | |
| 6,174,280 B1 | 1/2001 | Oneda et al. | |
| 6,190,330 B1 | 2/2001 | Harhen | |
| 6,214,028 B1 | 4/2001 | Yoon et al. | |
| 6,261,226 B1 | 7/2001 | McKenna et al. | |
| 6,261,307 B1 | 7/2001 | Yoon et al. | |
| 6,277,064 B1 | 8/2001 | Yoon | |
| 6,296,608 B1 | 10/2001 | Daniels et al. | |
| 6,301,047 B1 | 10/2001 | Hoshino et al. | |
| 6,350,231 B1 | 2/2002 | Ailinger et al. | |
| 6,369,855 B1 | 4/2002 | Chauvel et al. | |
| 6,375,653 B1 | 4/2002 | Desai | |
| 6,387,043 B1 | 5/2002 | Yoon | |
| 6,433,492 B1 | 8/2002 | Buonavita | |
| 6,454,702 B1 | 9/2002 | Smith | |
| 6,456,684 B1 | 9/2002 | Mun et al. | |
| 6,461,294 B1 | 10/2002 | Oneda et al. | |
| 6,464,633 B1 | 10/2002 | Hosoda et al. | |
| 6,482,149 B1 | 11/2002 | Torii | |
| 6,503,195 B1 | 1/2003 | Keller et al. | |
| 6,527,704 B1 | 3/2003 | Chang et al. | |
| 6,547,724 B1 | 4/2003 | Soble et al. | |
| 6,554,767 B2 | 4/2003 | Tanaka | |
| 6,564,088 B1 | 5/2003 | Soller et al. | |
| 6,640,017 B1 | 10/2003 | Tsai et al. | |
| 6,648,816 B2 | 11/2003 | Irion et al. | |
| 6,683,716 B1 * | 1/2004 | Costales | 359/465 |
| 6,687,010 B1 | 2/2004 | Horii et al. | |
| 6,697,536 B1 | 2/2004 | Yamada | |
| 6,699,180 B2 | 3/2004 | Kobayashi | |
| 6,736,773 B2 | 5/2004 | Wendlandt et al. | |
| 6,748,975 B2 | 6/2004 | Hartshorne et al. | |
| 6,796,939 B1 | 9/2004 | Hirata et al. | |
| 6,833,871 B1 | 12/2004 | Merrill et al. | |
| 6,845,190 B1 | 1/2005 | Smithwick et al. | |
| 6,891,977 B2 | 5/2005 | Gallagher | |
| 6,916,286 B2 | 7/2005 | Kazakevich | |
| 6,928,314 B1 | 8/2005 | Johnson et al. | |
| 6,929,636 B1 | 8/2005 | von Alten | |
| 6,947,784 B2 | 9/2005 | Zalis | |
| 6,951,536 B2 | 10/2005 | Yokoi et al. | |

(56) References Cited

U.S. PATENT DOCUMENTS

| | | |
|---|---|---|
| 6,965,702 B2 | 11/2005 | Gallagher |
| 6,966,906 B2 | 11/2005 | Brown |
| 6,974,240 B2 | 12/2005 | Takahashi |
| 6,974,411 B2 | 12/2005 | Belson |
| 6,992,694 B2 | 1/2006 | Abe |
| 6,997,871 B2 | 2/2006 | Sonnenschein et al. |
| 7,004,900 B2 | 2/2006 | Wendlandt et al. |
| 7,029,435 B2 | 4/2006 | Nakao |
| 7,041,050 B1 | 5/2006 | Ronald |
| 7,095,548 B1 | 8/2006 | Cho et al. |
| 7,103,228 B2 | 9/2006 | Kraft et al. |
| 7,116,352 B2 | 10/2006 | Yaron |
| 7,173,656 B1 | 2/2007 | Dunton et al. |
| 7,228,004 B2 | 6/2007 | Gallagher et al. |
| 7,258,663 B2 | 8/2007 | Doguchi et al. |
| 7,280,141 B1 | 10/2007 | Frank et al. |
| 7,317,458 B2 | 1/2008 | Wada |
| 7,322,934 B2 | 1/2008 | Miyake et al. |
| 7,341,555 B2 | 3/2008 | Ootawara et al. |
| 7,362,911 B1 | 4/2008 | Frank |
| 7,389,892 B2 | 6/2008 | Park |
| 7,405,877 B1 | 7/2008 | Schechterman |
| 7,435,218 B2 | 10/2008 | Krattiger et al. |
| 7,436,562 B2 | 10/2008 | Nagasawa et al. |
| 7,507,200 B2 | 3/2009 | Okada |
| 7,551,196 B2 | 6/2009 | Ono et al. |
| 7,556,599 B2 | 7/2009 | Rovegno |
| 7,561,190 B2 | 7/2009 | Deng et al. |
| 7,621,869 B2 | 11/2009 | Ratnakar |
| 7,646,520 B2 | 1/2010 | Funaki et al. |
| 7,678,043 B2 | 3/2010 | Gilad |
| 7,683,926 B2 | 3/2010 | Schechterman et al. |
| 7,749,156 B2 | 7/2010 | Ouchi |
| 7,825,964 B2 | 11/2010 | Hoshino et al. |
| 7,864,215 B2 | 1/2011 | Carlsson et al. |
| 7,910,295 B2 | 3/2011 | Hoon et al. |
| 7,927,272 B2 | 4/2011 | Bayer et al. |
| 8,009,167 B2 | 8/2011 | Dekel et al. |
| 8,064,666 B2 | 11/2011 | Bayer |
| 8,070,743 B2 | 12/2011 | Kagan et al. |
| 8,182,422 B2 | 5/2012 | Bayer et al. |
| 8,197,399 B2 | 6/2012 | Bayer et al. |
| 8,235,887 B2 | 8/2012 | Bayer et al. |
| 8,287,446 B2 | 10/2012 | Bayer |
| 8,289,381 B2 | 10/2012 | Bayer et al. |
| 8,310,530 B2 | 11/2012 | Bayer et al. |
| 8,587,645 B2 | 11/2013 | Bayer et al. |
| 2001/0007468 A1 | 7/2001 | Sugimoto et al. |
| 2001/0031912 A1 | 10/2001 | Adler |
| 2001/0037052 A1 | 11/2001 | Higuchi et al. |
| 2001/0051766 A1 | 12/2001 | Gazdzinski |
| 2001/0056238 A1 | 12/2001 | Tsujita |
| 2002/0026188 A1 | 2/2002 | Balbierz et al. |
| 2002/0039400 A1 | 4/2002 | Kaufman et al. |
| 2002/0089584 A1 | 7/2002 | Abe |
| 2002/0095168 A1* | 7/2002 | Griego et al. .......... 606/167 |
| 2002/0099267 A1 | 7/2002 | Wendlandt et al. |
| 2002/0101546 A1 | 8/2002 | Sharp et al. |
| 2002/0103420 A1 | 8/2002 | Coleman et al. |
| 2002/0110282 A1 | 8/2002 | Kraft et al. |
| 2002/0115908 A1 | 8/2002 | Farkas et al. |
| 2002/0156347 A1 | 10/2002 | Kim et al. |
| 2002/0165444 A1 | 11/2002 | Whitman |
| 2002/0193662 A1 | 12/2002 | Belson |
| 2003/0001951 A1 | 1/2003 | Tsujita et al. |
| 2003/0004399 A1 | 1/2003 | Belson |
| 2003/0011768 A1 | 1/2003 | Jung et al. |
| 2003/0032863 A1 | 2/2003 | Kazakevich |
| 2003/0040668 A1 | 2/2003 | Kaneko et al. |
| 2003/0045778 A1 | 3/2003 | Ohline et al. |
| 2003/0065250 A1 | 4/2003 | Chiel et al. |
| 2003/0088152 A1 | 5/2003 | Takada |
| 2003/0093031 A1 | 5/2003 | Long et al. |
| 2003/0093088 A1 | 5/2003 | Long et al. |
| 2003/0103199 A1 | 6/2003 | Jung et al. |
| 2003/0105386 A1 | 6/2003 | Voloshin et al. |
| 2003/0120130 A1 | 6/2003 | Glukhovsky |
| 2003/0125630 A1 | 7/2003 | Furnish |
| 2003/0125788 A1 | 7/2003 | Long |
| 2003/0130711 A1 | 7/2003 | Pearson et al. |
| 2003/0153866 A1 | 8/2003 | Long et al. |
| 2003/0161545 A1 | 8/2003 | Gallagher |
| 2003/0167007 A1 | 9/2003 | Belson |
| 2003/0171650 A1 | 9/2003 | Tartaglia et al. |
| 2003/0176767 A1 | 9/2003 | Long et al. |
| 2003/0179302 A1 | 9/2003 | Harada et al. |
| 2003/0187326 A1 | 10/2003 | Chang |
| 2003/0195545 A1 | 10/2003 | Hermann et al. |
| 2003/0197781 A1 | 10/2003 | Sugimoto et al. |
| 2003/0197793 A1 | 10/2003 | Mitsunaga et al. |
| 2003/0225433 A1 | 12/2003 | Nakao |
| 2003/0233115 A1 | 12/2003 | Eversull et al. |
| 2004/0015049 A1 | 1/2004 | Zaar |
| 2004/0023397 A1 | 2/2004 | Vig et al. |
| 2004/0034278 A1 | 2/2004 | Adams |
| 2004/0049096 A1 | 3/2004 | Adams |
| 2004/0059191 A1 | 3/2004 | Krupa et al. |
| 2004/0080613 A1 | 4/2004 | Moriyama |
| 2004/0085443 A1 | 5/2004 | Kallioniemi et al. |
| 2004/0097790 A1 | 5/2004 | Farkas et al. |
| 2004/0109164 A1 | 6/2004 | Horii et al. |
| 2004/0109319 A1 | 6/2004 | Takahashi |
| 2004/0111019 A1 | 6/2004 | Long |
| 2004/0122291 A1 | 6/2004 | Takahashi |
| 2004/0141054 A1 | 7/2004 | Mochida et al. |
| 2004/0158124 A1 | 8/2004 | Okada |
| 2004/0207618 A1 | 10/2004 | Williams et al. |
| 2004/0242987 A1 | 12/2004 | Liew et al. |
| 2005/0010084 A1 | 1/2005 | Tsai |
| 2005/0014996 A1 | 1/2005 | Konomura et al. |
| 2005/0020918 A1 | 1/2005 | Wilk et al. |
| 2005/0020926 A1 | 1/2005 | Wiklof et al. |
| 2005/0038317 A1 | 2/2005 | Ratnakar |
| 2005/0038319 A1 | 2/2005 | Goldwasser et al. |
| 2005/0068431 A1 | 3/2005 | Mori |
| 2005/0085693 A1 | 4/2005 | Belson et al. |
| 2005/0085790 A1 | 4/2005 | Guest et al. |
| 2005/0096502 A1 | 5/2005 | Khalili |
| 2005/0154278 A1 | 7/2005 | Cabiri et al. |
| 2005/0165272 A1 | 7/2005 | Okada et al. |
| 2005/0165279 A1 | 7/2005 | Adler et al. |
| 2005/0177024 A1 | 8/2005 | Mackin |
| 2005/0203420 A1 | 9/2005 | Kleen et al. |
| 2005/0215911 A1 | 9/2005 | Alfano et al. |
| 2005/0222500 A1 | 10/2005 | Itoi |
| 2005/0228224 A1 | 10/2005 | Okada et al. |
| 2005/0267361 A1 | 12/2005 | Younker et al. |
| 2005/0272975 A1 | 12/2005 | McWeeney et al. |
| 2005/0272977 A1 | 12/2005 | Saadat et al. |
| 2006/0044267 A1 | 3/2006 | Xie et al. |
| 2006/0052709 A1 | 3/2006 | DeBaryshe et al. |
| 2006/0058584 A1 | 3/2006 | Hirata |
| 2006/0106286 A1 | 5/2006 | Wendlandt et al. |
| 2006/0114986 A1 | 6/2006 | Knapp et al. |
| 2006/0149127 A1 | 7/2006 | Seddiqui et al. |
| 2006/0149129 A1 | 7/2006 | Watts et al. |
| 2006/0183975 A1 | 8/2006 | Saadat et al. |
| 2006/0184037 A1 | 8/2006 | Ince et al. |
| 2006/0217594 A1 | 9/2006 | Ferguson |
| 2006/0238614 A1 | 10/2006 | Konno |
| 2006/0252994 A1 | 11/2006 | Ratnakar |
| 2006/0279632 A1 | 12/2006 | Anderson |
| 2006/0285766 A1 | 12/2006 | Ali |
| 2006/0293562 A1 | 12/2006 | Uchimura et al. |
| 2007/0015967 A1 | 1/2007 | Boulais et al. |
| 2007/0015989 A1 | 1/2007 | Desai et al. |
| 2007/0066868 A1 | 3/2007 | Shikii |
| 2007/0083081 A1 | 4/2007 | Schlagenhauf et al. |
| 2007/0103460 A1 | 5/2007 | Zhang et al. |
| 2007/0142711 A1 | 6/2007 | Bayer et al. |
| 2007/0173686 A1 | 7/2007 | Lin et al. |
| 2007/0177008 A1 | 8/2007 | Bayer et al. |
| 2007/0183685 A1 | 8/2007 | Wada et al. |
| 2007/0185384 A1 | 8/2007 | Bayer et al. |

(56) References Cited

U.S. PATENT DOCUMENTS

| | | |
|---|---|---|
| 2007/0225552 A1 | 9/2007 | Segawa et al. |
| 2007/0225554 A1 | 9/2007 | Maseda et al. |
| 2007/0225734 A1 | 9/2007 | Bell et al. |
| 2007/0238927 A1 | 10/2007 | Ueno et al. |
| 2007/0244354 A1 | 10/2007 | Bayer |
| 2007/0270642 A1 | 11/2007 | Bayer et al. |
| 2007/0279486 A1 | 12/2007 | Bayer et al. |
| 2007/0280669 A1* | 12/2007 | Karim .................... 396/155 |
| 2007/0293720 A1 | 12/2007 | Bayer |
| 2008/0021269 A1 | 1/2008 | Tinkham et al. |
| 2008/0021274 A1 | 1/2008 | Bayer et al. |
| 2008/0033450 A1 | 2/2008 | Bayer et al. |
| 2008/0039693 A1 | 2/2008 | Karasawa |
| 2008/0064931 A1 | 3/2008 | Schena et al. |
| 2008/0065110 A1 | 3/2008 | Duval et al. |
| 2008/0071291 A1 | 3/2008 | Duval et al. |
| 2008/0079827 A1 | 4/2008 | Hoshino et al. |
| 2008/0084478 A1 | 4/2008 | Gilad et al. |
| 2008/0097292 A1 | 4/2008 | Cabiri et al. |
| 2008/0114288 A1 | 5/2008 | Whayne et al. |
| 2008/0130108 A1 | 6/2008 | Bayer et al. |
| 2008/0154288 A1 | 6/2008 | Belson |
| 2008/0199829 A1 | 8/2008 | Paley et al. |
| 2008/0200763 A1 | 8/2008 | Ueno |
| 2008/0275298 A1 | 11/2008 | Ratnakar |
| 2009/0015842 A1 | 1/2009 | Leitgeb et al. |
| 2009/0023998 A1 | 1/2009 | Ratnakar |
| 2009/0028407 A1 | 1/2009 | Seibel et al. |
| 2009/0036739 A1 | 2/2009 | Hadani |
| 2009/0049627 A1 | 2/2009 | Kritzler |
| 2009/0082629 A1 | 3/2009 | Dotan et al. |
| 2009/0105538 A1 | 4/2009 | Van Dam et al. |
| 2009/0137867 A1 | 5/2009 | Goto |
| 2009/0208071 A1 | 8/2009 | Nishimura et al. |
| 2009/0213211 A1 | 8/2009 | Bayer et al. |
| 2009/0231419 A1 | 9/2009 | Bayer |
| 2010/0217076 A1 | 8/2010 | Ratnakar |
| 2011/0160535 A1 | 6/2011 | Bayer et al. |
| 2011/0213206 A1 | 9/2011 | Boutillette et al. |
| 2012/0033062 A1 | 2/2012 | Bayer |
| 2012/0053407 A1 | 3/2012 | Levy |
| 2012/0065468 A1 | 3/2012 | Levy et al. |
| 2012/0209071 A1 | 8/2012 | Bayer et al. |
| 2012/0224026 A1 | 9/2012 | Bayer et al. |
| 2012/0229615 A1 | 9/2012 | Kirma et al. |
| 2012/0232340 A1 | 9/2012 | Levy et al. |
| 2012/0232343 A1 | 9/2012 | Levy et al. |
| 2012/0232345 A1 | 9/2012 | Levy et al. |
| 2012/0300999 A1 | 11/2012 | Bayer |
| 2013/0012778 A1 | 1/2013 | Bayer et al. |
| 2013/0116506 A1 | 5/2013 | Bayer et al. |
| 2014/0018624 A1 | 1/2014 | Bayer et al. |
| 2014/0046136 A1 | 2/2014 | Bayer et al. |

FOREIGN PATENT DOCUMENTS

| | | |
|---|---|---|
| DE | 196 26433 | 1/1998 |
| DE | 20 2006 017 173 U1 | 3/2007 |
| EP | 0 586 162 | 3/1994 |
| EP | 1 570 778 A1 | 9/2005 |
| EP | 1 769 720 A1 | 4/2007 |
| FR | 711 949 | 9/1931 |
| JP | 49-130235 A | 12/1974 |
| JP | 56-9712 A | 1/1981 |
| JP | 56-56486 A | 5/1981 |
| JP | 57-170707 | 10/1982 |
| JP | 60-83636 A | 5/1985 |
| JP | 60-111217 A | 6/1985 |
| JP | 62-094312 U1 | 6/1987 |
| JP | 63-309912 A | 12/1988 |
| JP | 1-267514 A | 10/1989 |
| JP | 1-172847 U | 12/1989 |
| JP | 2-295530 A | 12/1990 |
| JP | 3-159629 A | 7/1991 |
| JP | 4-500768 A | 2/1992 |
| JP | 4-341232 A | 11/1992 |
| JP | 5-285091 A | 11/1993 |
| JP | 5-307144 A | 11/1993 |
| JP | 5-341210 A | 12/1993 |
| JP | 6-9228 B2 | 2/1994 |
| JP | 60-76714 A | 3/1994 |
| JP | 6-130308 A | 5/1994 |
| JP | 6-169880 A | 6/1994 |
| JP | 7-352 A | 1/1995 |
| JP | 7-354 A | 1/1995 |
| JP | 7-021001 U | 4/1995 |
| JP | 7-275197 A | 10/1995 |
| JP | 8-024208 A2 | 1/1996 |
| JP | 8-206061 A | 8/1996 |
| JP | 9-56662 A | 3/1997 |
| JP | 7-136108 A | 5/1998 |
| JP | 11-76150 A | 3/1999 |
| JP | 11-253401 A | 9/1999 |
| JP | 11332821 | 12/1999 |
| JP | 2003-135388 A | 5/2003 |
| JP | 2003-220023 A | 8/2003 |
| JP | 2004-202252 A | 7/2004 |
| JP | 2004-525717 A | 8/2004 |
| JP | 2004-537362 A | 12/2004 |
| JP | 2007-143580 A | 6/2007 |
| WO | WO 93/15648 | 8/1993 |
| WO | WO-99/17542 A1 | 4/1999 |
| WO | WO-99/30506 A1 | 6/1999 |
| WO | WO 02/085194 | 10/2002 |
| WO | WO-02/094105 A2 | 11/2002 |
| WO | WO-02/094105 A3 | 11/2002 |
| WO | WO-03/013349 A2 | 2/2003 |
| WO | WO-03/013349 A3 | 2/2003 |
| WO | WO-2006/073676 A1 | 7/2006 |
| WO | WO-2006/073725 A1 | 7/2006 |
| WO | WO-2006/087981 A1 | 8/2006 |
| WO | WO-2006/110275 A2 | 10/2006 |
| WO | WO-2006/110275 A3 | 10/2006 |
| WO | WO-2007/015241 A2 | 2/2007 |
| WO | WO-2007/015241 A3 | 2/2007 |
| WO | WO-2007/070644 A2 | 6/2007 |
| WO | WO-2007/070644 A3 | 6/2007 |
| WO | WO-2007/087421 A2 | 8/2007 |
| WO | WO-2007/087421 A3 | 8/2007 |
| WO | WO-2007/092533 A2 | 8/2007 |
| WO | WO-2007/092636 A2 | 8/2007 |
| WO | WO-2007/092636 A3 | 8/2007 |
| WO | WO-2007/136859 A2 | 11/2007 |
| WO | WO-2007/136859 A3 | 11/2007 |
| WO | WO-2007/136879 A2 | 11/2007 |
| WO | WO-2007/136879 A3 | 11/2007 |
| WO | WO-2007/136879 B1 | 11/2007 |
| WO | WO-2009/014895 A1 | 1/2009 |
| WO | WO-2009/015396 A2 | 1/2009 |
| WO | WO-2009/015396 A3 | 1/2009 |
| WO | WO-2009/049322 A2 | 4/2009 |
| WO | WO-2009/049322 A3 | 4/2009 |
| WO | WO-2009/049324 A1 | 4/2009 |
| WO | WO-2009/062179 A1 | 5/2009 |

OTHER PUBLICATIONS

Invitation to Pay Additional Fees for PCT/US2007/003631, filed Feb. 9, 2007, mailed Aug. 7, 2007, 5 pgs.

Invitation to Pay Additional Fees for PCT/US2007/003322, filed Feb. 6, 2007, mailed Aug. 7, 2007, 6 pgs.

U.S. Appl. No. 11/828,835, filed Jun. 14, 2005, Bayer.

U.S. Appl. No. 11/834,540, filed Aug. 6, 2007, Bayer.

International Search Report for PCT/US2008/069435, filed Jul. 8, 2008, mailed Oct. 23, 2008, 8 pgs.

Invitation to Pay Additional Fees for PCT/US2008/071390, filed Jul. 28, 2008, mailed Nov. 11, 2008, 5 pgs.

U.S. Appl. No. 11/153,007, filed Jun. 14, 2005, Seddiqui et al.

U.S. Appl. No. 11/160,646, filed Jul. 1, 2005, Desai et al.

U.S. Appl. No. 11/215,660, filed Aug. 29, 2005, Watts et al.

U.S. Appl. No. 11/609,838, filed Dec. 12, 2006, Bayer et al.

U.S. Appl. No. 11/626,189, filed Jan. 23, 2007, Bayer et al.

(56) References Cited

OTHER PUBLICATIONS

U.S. Appl. No. 11/672,020, filed Feb. 6, 2007, Bayer et al.
U.S. Appl. No. 11/736,438, filed Apr. 17, 2007, Bayer.
U.S. Appl. No. 11/751,596, filed May 21, 2007, Bayer.
U.S. Appl. No. 11/751,597, filed May 21, 2007, Bayer et al.
U.S. Appl. No. 11/751,605, filed May 21, 2007, Diel et al.
International Search Report for PCT/US2005/044624, filed Dec. 8, 2005, mailed May 19, 2006, 16 pgs.
International Search Report for PCT/US2006/047748, filed Dec. 13, 2006, mailed Jun. 20, 2007, 12 pgs.
Advisory Action mailed on Nov. 2, 2010, for U.S. Appl. No. 11/609,838, filed Dec. 12, 2006, 3 pages.
Advisory Action mailed on May 23, 2011, for U.S. Appl. No. 11/751,605, filed May 21, 2007, 3 pages.
Amendment in Response to Non-Final Office Action filed on Jun. 29, 2009, for U.S. Appl. No. 11/215,660, filed Aug. 29, 2005, 9 pages.
Amendment in Response to Final Office Action filed on Mar. 8, 2010, for U.S. Appl. No. 11/215,660, filed Aug. 29, 2005, 11 pages.
Amendment in Response to Non-Final Office Action filed on Aug. 30, 2010, for U.S. Appl. No. 11/215,660, filed Aug. 29, 2005, 17 pages.
Amendment in Response to Final Office Action filed on Oct. 22, 2010, for U.S. Appl. No. 11/609,838, filed Dec. 12, 2006, 15 pages.
Amendment in Response to Non-Final Office Action filed on Oct. 22, 2010, for U.S. Appl. No. 11/834,540, filed Aug. 6, 2007, 13 pages.
Amendment in Response to Non-Final Office Action filed on Feb. 9, 2011, for U.S. Appl. No. 11/828,835, filed Jul. 26, 2007, 10 pages.
Amendment in Response to Non-Final Office Action filed on Feb. 25, 2011, for U.S. Appl. No. 11/751,605, filed May 21, 2007, 15 pages.
Amendment in Response to Final Office Action filed on Feb. 28, 2011, for U.S. Appl. No. 11/215,660, filed Aug. 29, 2005, 11 pages.
Amendment in Response to Non-Final Office Action filed on Apr. 12, 2011, for U.S. Appl. No. 11/626,189, filed Jan. 23, 2007, 18 pages.
Amendment in Response to Non-Final Office Action filed on May 17, 2011, for U.S. Appl. No. 11/609,838, filed Dec. 12, 2006, 18 pages.
Amendment in Response to Final Office Action filed on May 17, 2011, for U.S. Appl. No. 11/751,605, filed May 21, 2007, 10 pages.
Amendment in Response to Final Office Action filed on May 24, 2011, for U.S. Appl. No. 11/828,835, filed Jul. 26, 2007, 13 pages.
Amendment in Response to Non-Final Office Action filed on May 24, 2011, for U.S. Appl. No. 11/736,438, filed Apr. 17, 2007, 11 pages.
Amendment in Response to Non-Final Office Action filed on Jun. 6, 2011, for U.S. Appl. No. 12/101,050, filed Apr. 10, 2008, 17 pages.
Amendment in Response to Final Office Action filed on Jun. 7, 2011, for U.S. Appl. No. 11/751,605, filed May 21, 2007, 11 pages.
Amendment in Response to Final Office Action filed on Dec. 7, 2011, for U.S. Appl. No. 11/736,438, filed Apr. 17, 2007, 10 pages.
Amendment in Response to Non-Final Office Action filed on Dec. 16, 2011, for U.S. Appl. No. 11/938,256, filed Nov. 10, 2007, 10 pages.
Amendment in Response to Non-Final Office Action filed on Jan. 9, 2012, for U.S. Appl. No. 11/751,596, filed May 21, 2007, 9 pages.
Amendment in Response to Non-Final Office Action filed on Feb. 15, 2012, for U.S. Appl. No. 11/626,189, filed Jan. 23, 2007, 13 pages.
Amendment in Response to Non-Final Office Action filed on Feb. 17, 2012, for U.S. Appl. No. 11/751,597, filed May 21, 2007, 18 pages.
European Communication mailed on Jan. 22, 2009, for European Application No. 07777255.6, filed on May 21, 2007, 2 pages.
European Office Action mailed on May 5, 2009, for European Patent Application No. 07763368.3, filed on Feb. 6, 2007, 3 pages.
European Office Action mailed on Feb. 5, 2010, for European Patent Application No. 06845440.4, filed on Dec. 13, 2006, 4 pages.
European Office Action mailed on Apr. 1, 2010, for European Patent Application No. 07717235.1, filed on Feb. 9, 2007, 2 pages.
European Office Action mailed on Nov. 8, 2010, for European Patent Application No. 05854262.2, filed on Dec. 8, 2005, 5 pages.
European Office Action mailed on Jun. 14, 2011, for European Patent Application No. 07795177.0, filed on May 21, 2007, 6 pages.
Final Office Action mailed on Oct. 8, 2009, for U.S. Appl. No. 11/215,660, filed Aug. 29, 2005, 12 pages.
Final Office Action mailed on Aug. 23, 2010, for U.S. Appl. No. 11/609,838, filed Dec. 12, 2006, 20 pages.
Final Office Action mailed on Nov. 1, 2010, for U.S. Appl. No. 11/215,660, filed Aug. 29, 2005, 12 pages.
Final Office Action mailed on Mar. 22, 2011, for U.S. Appl. No. 11/828,835, filed Jul. 26, 2007, 11 pages.
Final Office Action mailed on Apr. 29, 2011, for U.S. Appl. No. 11/751,605, filed May 21, 2007, 9 pages.
Final Office Action mailed on Aug. 3, 2011, for U.S. Appl. No. 11/736,438, filed Apr. 17, 2007, 11 pages.
International Search Report mailed on May 18, 2006, for PCT Patent Application No. PCT/US2005/045499, filed on Dec. 8, 2005, 4 pages.
International Search Report mailed on Sep. 28, 2007, for PCT Patent Application No. PCT/US2007/002096 filed on Jan. 23, 2007, 4 pages.
International Search Report mailed on Oct. 25, 2007, for PCT Patent Application No. PCT/US2007/003322, filed on Feb. 6, 2007, 5 pages.
International Search Report mailed on Oct. 26, 2007, for PCT Patent Application No. PCT/US2007/003631, filed on Feb. 9, 2007, 5 pages.
International Search Report mailed on Dec. 11, 2007, for PCT Patent Application No. PCT/US2007/012358, filed on May 21, 2007, 3 pages.
International Search Report mailed on Jan. 28, 2008, for PCT Patent Application No. PCT/US2007/012189, filed on May 21, 2007, 2 pages.
International Search Report mailed on Feb. 25, 2009, for PCT Patent Application No. PCT/US2008/071390, filed on Jul. 28, 2008, 2 pages.
International Search Report mailed on Mar. 13, 2009, for PCT Patent Application No. PCT/US2008/083034, filed on Nov. 10, 2008, 3 pages.
International Search Report mailed on Mar. 13, 2009, for PCT Patent Application No. PCT/US2008/079891, filed on Nov. 10, 2008, 2 pages.
International Search Report mailed on Apr. 6, 2009, for PCT Patent Application No. PCt/US2008/079878, filed on Oct. 14, 2008, 3 pages.
Invitation to Pay Additional Fees mailed on Dec. 29, 2008, for PCT Patent Application No. PCT/US2008/079891, filed on Oct. 14, 2008, 7 pages.
Japanese Office Action mailed on Jul. 19, 2011, for Japanese Patent Application No. 2007-550378, filed on Dec. 8, 2005, with English Translation, 11 pages.
Non-Final Office Action mailed on Jan. 10, 2008, for U.S. Appl. No. 11/160,646, filed Jul. 1, 2005, 6 pages.
Non-Final Office Action mailed on Mar. 12, 2008, for U.S. Appl. No. 11/153,007, filed Jun. 14, 2005, 11 pages.
Non-Final Office Action mailed on Mar. 25, 2009, for U.S. Appl. No. 11/215,660, filed Aug. 29, 2005, 11 pages.
Non-Final Office Action mailed on Mar. 29, 2010, for U.S. Appl. No. 11/215,660, filed Aug. 29, 2005, 16 pages.
Non-Final Office Action mailed on Apr. 6, 2010, for U.S. Appl. No. 11/609,838, filed Dec. 12, 2006, 25 pages.
Non-Final Office Action mailed on Aug. 24, 2010, for U.S. Appl. No. 11/834,540, filed Aug. 6, 2007, 11 pages.
Non-Final Office Action mailed on Oct. 18, 2010, for U.S. Appl. No. 11/626,189, filed Jan. 23, 2007, 11 pages.
Non-Final Office Action mailed on Oct. 28, 2010, for U.S. Appl. No. 11/828,835, filed Jul. 26, 2007, 11 pages.
Non-Final Office Action mailed on Dec. 22, 2010, for U.S. Appl. No. 11/751,605, filed May 21, 2007, 10 pages.
Non-Final Office Action mailed on Feb. 17, 2011, for U.S. Appl. No. 11/609,838, filed Dec. 12, 2006, 24 pages.
Non-Final Office Action mailed on Mar. 2, 2011, for U.S. Appl. No. 11/736,438, filed Apr. 17, 2007, 10 pages.
Non-Final Office Action mailed on May 23, 2011, for U.S. Appl. No. 12/101,050, filed Apr. 10, 2008, 11 pages.
Non-Final Office Action mailed on Jun. 28, 2011, for U.S. Appl. No. 11/938,256, filed Nov. 10, 2007, 23 pages.
Non-Final Office Action mailed on Aug. 4, 2011, for U.S. Appl. No. 11/609,838, filed Dec. 12, 2006, 16 pages.

(56) References Cited

OTHER PUBLICATIONS

Non-Final Office Action mailed on Aug. 15, 2011, for U.S. Appl. No. 11/626,189, filed Jan. 23, 2007, 13 pages.
Non-Final Office Action mailed on Aug. 18, 2011, for U.S. Appl. No. 11/751,597, filed May 21, 2007, 25 pages.
Non-Final Office Action mailed on Sep. 9, 2011, for U.S. Appl. No. 11/751,596, filed May 21, 2007, 6 pages.
Non-Final Office Action mailed on Oct. 21, 2011, for PCT U.S. Appl. No. 12/251,406, filed Oct. 14, 2008, 8 pages.
Non-Final Office Action mailed on Nov. 23, 2011, for U.S. Appl. No. 11/672,020, filed Feb. 6, 2007, 12 pages.
Non-Final Office Action mailed on Feb. 13, 2012, for U.S. Appl. No. 13/275,206, filed Oct. 17, 2011, 13 pages.
Non-Final Office Action mailed on Feb. 14, 2012, for U.S. Appl. No. 12/251,383, filed Oct. 14, 2008, 9 pages.
Notice of Allowance mailed on Dec. 13, 2010, for U.S. Appl. No. 11/834,540, filed Aug. 6, 2007, 4 pages.
Notice of Allowance mailed on Jul. 22, 2011, for U.S. Appl. No. 12/101,050, filed Apr. 10, 2008, 7 pages.
Notice of Allowance mailed on Feb. 8, 2012, for U.S. Appl. No. 11/609,838, filed Dec. 12, 2006, 8 pages.
Preliminary Amendment filed Jan. 26, 2009, for U.S. Appl. No. 11/672,020, filed Feb. 6, 2007, 11 pages.
Response to European Communication filed Feb. 6, 2009, for European Patent Application No. 07777255.6, filed on May 21, 2007, 5 pages.
Response to European Office Action filed on Nov. 11, 2009, for European Patent Application No. 07783368.3, filed on Feb. 6, 2007, 12 pages.
Response to European Office Action filed on Jul. 7, 2010, for European Patent Application No. 06845440.4, filed on Dec. 13, 2006, 13 pages.
Response to European Office Action filed on Aug. 18, 2010, for European Patent Application No. 07717235.1, filed on Feb. 9, 2007, 7 pages.
Response to European Office Action filed on Mar. 8, 2011, for European Patent Application No. 05854262.2, filed on Dec. 8, 2005, 11 pages.
Response to European Office Action filed on Dec. 13, 2011, for European Patent Application No. 07795177.0, filed on May 21, 2007, 9 pages.
Response to Restriction Requirement filed on Jan. 26, 2009, for U.S. Appl. No. 11/215,660, filed Aug. 29, 2005, 2 pages.
Response to Restriction Requirement filed on Jul. 23, 2010, for U.S. Appl. No. 11/751,605, filed May 21, 2007, 9 pages.
Response to Restriction Requirement filed on Aug. 4, 2010, for U.S. Appl. No. 11/834,540, filed Aug. 6, 2007, 5 pages.
Response to Restriction Requirement filed on Sep. 9, 2010, for U.S. Appl. No. 11/626,189, filed Jan. 23, 2007, 8 pages.
Response to Restriction Requirement filed on Oct. 21, 2010, for U.S. Appl. No. 11/828,835, filed Jul. 26, 2007, 7 pages.
Response to Restriction Requirement filed on Feb. 8, 2011, for U.S. Appl. No. 11/736,438, filed Apr. 17, 2007, 8 pages.
Response to Restriction Requirement filed on Apr. 27, 2011, for U.S. Appl. No. 12/101,050, filed Apr. 10, 2008, 11 pages.
Response to Restriction Requirement filed on Jun. 16, 2011, for U.S. Appl. No. 11/751,596, filed May 21, 2007, 8 pages.
Response to Restriction Requirement filed on Oct. 31, 2011, for U.S. Appl. No. 11/672,020, filed Feb. 6, 2007, 3 pages.
Restriction Requirement mailed on Oct. 30, 2008, for U.S. Appl. No. 11/215,660, filed Aug. 29, 2005, 7 pages.
Restriction Requirement mailed on Jun. 25, 2010, for U.S. Appl. No. 11/751,605, filed May 21, 2007, 9 pages.
Restriction Requirement mailed on Jul. 13, 2010, for U.S. Appl. No. 11/834,540, filed Aug. 6, 2007, 8 pages.
Restriction Requirement mailed on Aug. 10, 2010, for U.S. Appl. No. 11/626,189, filed Jan. 23, 2007, 5 pages.
Restriction Requirement mailed on Sep. 21, 2010, for U.S. Appl. No. 11/828,835, filed Jul. 26, 2007, 6 pages.
Restriction Requirement mailed on Dec. 10, 2010, for U.S. Appl. No. 11/736,438, filed Apr. 17, 2007, 16 pages.
Restriction Requirement mailed on Mar. 11, 2011, for U.S. Appl. No. 12/101,050, filed Apr. 10, 2008, 6 pages.
Restriction Requirement mailed on Jun. 6, 2011, for U.S. Appl. No. 11/751,596, filed May 21, 2007, 6 pages.
Restriction Requirement mailed on Sep. 29, 2011, for U.S. Appl. No. 11/672,020, filed Feb. 6, 2007, 6 pages.
Restriction Requirement mailed on Nov. 28, 2011, for U.S. Appl. No. 12/251,383, filed Oct. 14, 2008, 6 pages.
Substitute Preliminary Amendment filed Mar. 8, 2010, for U.S. Appl. No. 11/672,020, filed Feb. 6, 2007, 2 pages.
Written Opinion of the International Searching Authority mailed on May 18, 2006, for PCT Patent Application No. PCT/US2005/045499, filed on Dec. 8, 2005, 9 pages.
Written Opinion of the International Searching Authority mailed on May 19, 2006, for PCT Patent Application No. PCT/US2005/044624, filed on Dec. 8, 2005, 8 pages.
Written Opinion of the International Searching Authority mailed on Jun. 20, 2007, for PCT Patent Application No. PCT/US2006/047748, filed on Dec. 13, 2006, 7 pages.
Written Opinion of the International Searching Authority mailed on Sep. 28, 2007, for PCT Patent Application No. PCT/US2007/002096 filed on Jan. 23, 2007, 8 pages.
Written Opinion of the International Searching Authority mailed on Oct. 25, 2007, for PCT Patent Application No. PCT/US2007/003322, filed on Feb. 6, 2007, 9 pages.
Written Opinion of the International Searching Authority mailed on Oct. 26, 2007, for PCT Patent Application No. PCT/US2007/003631, filed on Feb. 9, 2007, 7 pages.
Written Opinion of the International Searching Authority mailed on Dec. 11, 2007, for PCT Patent Application No. PCT/US2007/012358, filed on May 21, 2007, 6 pages.
Written Opinion of the International Searching Authority mailed on Jan. 28, 2008, for PCT Patent Application No. PCT/US2007/012189, filed on May 21, 2007, 7 pages.
Written Opinion of the International Searching Authority mailed on Oct. 23, 2008, for PCT Patent Application No. PCT/US2008/069435, filed on Jul. 8, 2008, 6 pages.
Written Opinion of the International Searching Authority mailed on Feb. 25, 2009, for PCT Patent Application No. PCT/US2008/071390, filed on Jul. 28, 2008, 7 pages.
Written Opinion of the International Searching Authority mailed on Mar. 13, 2009, for PCT Patent Application No. PCT/US2008/083034, filed on Nov. 10, 2008, 4 pages.
Written Opinion of International Searching Authority mailed on Mar. 13, 2009, for PCT Patent Application No. PCT/US2008/079891, filed on Nov. 10, 2008, 5 pages.
Written Opinion of International Searching Authority mailed on Apr. 6, 2009, for PCT Patent Application No. PCT/US2008/079878, filed on Oct. 14, 2008, 13 pages.
Amendment in Response to Non-Final Office Action filed on Jun. 25, 2010, for U.S. Appl. No. 11/609,838, filed Dec. 12, 2006, 14 pages.
Amendment in Response to Non-Final Office Action filed on Mar. 23, 2012, for U.S. Appl. No. 11/672,020, filed Feb. 6, 2007, 12 pages.
European Office Action mailed on May 21, 2012, for European Patent Application No. 06845440.4, filed on Jul. 10, 2008, 6 pages.
European Office Action mailed on May 21, 2012, for European Patent Application No. 07717024.9, filed on Aug. 21, 2008, 5 pages.
European Office Action mailed on May 21, 2012, for European Patent Application No. 07717235.1, filed on Sep. 5, 2008, 5 pages.
Extended European Search Report mailed Apr. 26, 2012, for European Patent Application No. 12153946.4, filed Feb. 3, 2012, 6 pages.
Extended European Search Report mailed Oct. 5, 2012, for European Patent Application No. 12162806.9, filed on Apr. 2, 2012, 5 pages.
Final Office Action mailed on Apr. 23, 2012, for U.S. Appl. No. 11/938,256, filed Nov. 10, 2007, 13 pages.
Final Office Action mailed on Apr. 25, 2012, for U.S. Appl. No. 12/251,406, filed Oct. 14, 2008, 10 pages.
Japanese Office Action mailed Feb. 28, 2012, for Japanese Patent Application No. 2008-545817, filed on Dec. 13, 2006, with English Translation, 6 pages.

(56) References Cited

OTHER PUBLICATIONS

Japanese Office Action mailed Jan. 8, 2013 for Japanese Patent Application No. 2008-545817, filed on Dec. 13, 2006, with English Translation, 6 pages.
Japanese Office Action mailed on Feb. 28, 2012, for Japanese Patent Application No. 2008-551487, filed on Jan. 23, 2007, with English Translation, 9 pages.
Japanese Office Action mailed on Feb. 28, 2012, for Japanese Patent Application No. 2008-554410, filed on Feb. 9, 2007, 6 pages.
Japanese Office Action mailed on Mar. 6, 2012, for Japanese Patent Application No. 2008-553430, filed on Feb. 6, 2007, with English Translation, 6 pages.
Notice of Allowance mailed on Feb. 29, 2012, for U.S. Appl. No. 11/751,596, filed May 21, 2007, 10 pages.
Notice of Allowance mailed on Mar. 14, 2012, for U.S. Appl. No. 11/626,189, filed Jan. 23, 2007, 13 pages.
Notice of Allowance mailed on Jun. 7, 2012, for U.S. Appl. No. 11/751,597, filed May 21, 2007, 17 pages.
Non-Final Office Action mailed on Jun. 22, 2012, for U.S. Appl. No. 12/181,280, filed Jun. 22, 2012, 12 pages.
Final Office Action mailed on Mar. 6, 2014, for U.S. Appl. No. 11/751,605, filed May 21, 2007, 8 pages.
Final Office Action mailed on Apr. 16, 2014, for U.S. Appl. No. 13/584,647, filed Aug. 13, 2012, 15 pages.
Final Office Action mailed on Jun. 10, 2014, for U.S. Appl. No. 11/215,660, filed Aug. 29, 2005, 14 pages.
Non-Final Office Action mailed on Jun. 11, 2014, for U.S. Appl. No. 13/463,690, filed May 3, 2012, 13 pages.
Notice of Allowance mailed on Mar. 3, 2014, for U.S. Appl. No. 11/938,256, filed Nov. 10, 2007, 5 pages.
Japanese Office Action mailed on Jan. 15, 2013, for Japanese Patent Application No. 2010-518438, filed on Jan. 25, 2010, with English Translation, 10 pages.
Japanese Office Action mailed on Mar. 5, 2013, for Japanese Patent Application No. 2008-553430, filed on Feb. 6, 2007, with English Translation, 4 pages.
Non-Final Office Action mailed on May 14, 2013, for U.S. Appl. No. 11/751,605, filed May 21, 2007, 11 pages.
Non-Final Office Action mailed on Jul. 19, 2013, for U.S. Appl. No. 11/938,256, filed Nov. 10, 2007, 12 pages.
Non-Final Office Action mailed on Sep. 5, 2013, for U.S. Appl. No. 13/454,974, filed Apr. 24, 2012, 11 pages.
Non-Final Office Action mailed on Sep. 20, 2013, for U.S. Appl. No. 13/584,647, filed Aug. 13, 2012, 13 pages.
Non-Final Office Action mailed on Nov. 14, 2013, for U.S. Appl. No. 11/215,660, filed Aug. 29, 2005, 10 pages.
Notice of Allowance mailed on Jul. 19, 2013, for U.S. Appl. No. 13/606,465, filed Sep. 7, 2012, 14 pages.
Restriction Requirement mailed on Jun. 21, 2013, for U.S. Appl. No. 13/454,974, filed Apr. 24, 2012, 11 pages.
Restriction Requirement mailed on Feb. 20, 2014, for U.S. Appl. No. 13/463,690, filed May 3, 2012, 6 pages.

\* cited by examiner

ENDOSCOPE ASSEMBLY WITH A POLARIZING FILTER

This application claims the benefit of U.S. Provisional Patent Application No. 60/772,442, filed Feb. 9, 2006, the entire disclosure of which is incorporated herein by reference.

This application is a continuation-in-part application of U.S. patent application Ser. No. 11/672,020, filed Feb. 6, 2007, the entire disclosure of which is incorporated herein by reference.

This application is a continuation-in-part application of U.S. patent application Ser. No. 11/626,189, filed Jan. 23, 2007, the entire disclosure of which is incorporated herein by reference.

This application is a continuation-in-part application of U.S. patent application Ser. No. 11/609,838, filed Dec. 12, 2006, the entire disclosure of which is incorporated herein by reference.

This application is a continuation-in-part application of U.S. patent application Ser. No. 11/215,660, filed Aug. 29, 2005, the entire disclosure of which is incorporated herein by reference.

This application is a continuation-in-part application of U.S. patent application Ser. No. 11/030,559, filed Jan. 5, 2005, the entire disclosure of which is incorporated herein by reference.

TECHNICAL FIELD OF THE INVENTION

The present invention relates to an endoscope assembly with a polarizing filter.

BACKGROUND OF THE INVENTION

A conventional endoscope is a medical device comprising a flexible tube, and a camera and a light source mounted on the distal end of the flexible tube. The endoscope is insertable into an internal body cavity through a body orifice to examine the body cavity and tissues for diagnosis. The tube of the endoscope has one or more longitudinal channels, through which an instrument can reach the body cavity to take samples of suspicious tissues or to perform other surgical procedures such as polypectomy.

There are many types of endoscopes, and they are named in relation to the organs or areas with which they are used. For example, gastroscopes are used for examination and treatment of the esophagus, stomach and duodenum; colonoscopes for the colon; bronchoscopes for the bronchi; laparoscopes for the peritoneal cavity; sigmoidoscopes for the rectum and the sigmoid colon; arthroscopes for joints; cystoscopes for the urinary bladder; and angioscopes for the examination of blood vessels.

Each endoscope has a single forward viewing camera mounted at the distal end of the flexible tube to transmit an image to an eyepiece or video camera at the proximal end. The camera is used to assist a medical professional in advancing the endoscope into a body cavity and looking for abnormalities. The camera provides the medical professional with a two-dimensional view from the distal end of the endoscope. To capture an image from a different angle or in a different portion, the endoscope must be repositioned or moved back and forth. Repositioning and movement of the endoscope prolongs the procedure and causes added discomfort, complications, and risks to the patient. Additionally, in an environment similar to the lower gastrointestinal tract, flexures, tissue folds and unusual geometries of the organ may prevent the endoscope's camera from viewing all areas of the organ. The unseen area may cause a potentially malignant (cancerous) polyp to be missed.

This problem can be overcome by providing an auxiliary camera and an auxiliary light source. The auxiliary camera and light source can be oriented to face the main camera and light source, thus providing an image of areas not viewable by the endoscope's main camera. This arrangement of cameras and light sources can provide both front and rear views of an area or an abnormality. In the case of polypectomy where a polyp is excised by placing a wire loop around the base of the polyp, the camera arrangement allows better placement of the wire loop to minimize damage to the adjacent healthy tissue.

Since the main camera and light source face the auxiliary camera and light source, the main light source interferes with the auxiliary camera, and the auxiliary light source interferes with the main camera. Light interference is the result of the light from a light source being projected directly onto the lens of a camera. This may cause light glare, camera blooming, or over saturation of light, resulting in inferior image quality.

Additionally, because of space constraint, the auxiliary camera and auxiliary light source are typically smaller than the main camera and main light source and use different technologies. Different types of cameras often require different levels of illumination. For example, the main camera generally requires a higher level of illumination and needs a more powerful light source. As a result, the auxiliary camera is often exposed to a significant amount of glare caused by the powerful main light source.

Therefore, there is a need to reduce or prevent light interference between the main camera and main light source and the auxiliary camera and auxiliary light source.

SUMMARY OF THE INVENTION

It is an object of this invention to address the problem of light interference involving the use of imaging devices and light sources for endoscopes. According to one aspect of the invention, the solution lies in the use of one or more polarizing filters including one or more linear or circular polarizing filters.

In accordance with one aspect of the invention, an endoscope assembly includes an imaging device, a light source, and a polarizing filter disposed in front of the light source. Preferably, the light source is positioned to illuminate a field of view of the imaging device. In a preferred embodiment, the endoscope assembly further includes a second polarizing filter disposed in front of the imaging device. Preferably, the planes of polarization of the first and second polarizing filters are aligned. A polarizing filter may be disposed on a cap or in a lens assembly of the imaging device.

In accordance with another aspect of the invention, an endoscope assembly includes an imaging device, a light source, and a polarizing filter disposed in front of the imaging device.

In accordance with still another aspect of the invention, an endoscope assembly includes an imaging device, a light source, and a polarizing filter disposed in front of both the imaging device and the light source.

In accordance with yet another aspect of the invention, an endoscope assembly includes an imaging device, a first polarizing filter disposed in front of the imaging device, a light source; and a second polarizing filter disposed in front of the light source. The plane of polarization of the first polarizing filter is at a substantially 90° angle from the plane of polarization of the second polarizing filter. Preferably, the light source faces the imaging device so that light from the light source is projected onto the imaging device.

In a preferred embodiment, the endoscope assembly further includes a second imaging device, a third polarizing filter disposed in front of the second imaging device, a second light source, and a fourth polarizing filter disposed in front of the second light source. The plane of polarization of the third polarizing filter is at a substantially 90° angle from the plane of polarization of the fourth polarizing filter.

In another preferred embodiment, the first light source faces the first imaging device, and the second light source faces the second imaging device.

In a further preferred embodiment, the second light source is positioned to illuminate a field of view of the first imaging device, and the first light source is positioned to illuminate a field of view of the second imaging device.

Preferably, the first imaging device and second light source are mounted on an insertion tube, and the second imaging device and first light source are mounted on an imaging assembly. The insertion tube may a channel, and a portion of the imaging assembly may be rotatably disposed inside the channel of the insertion tube with the second imaging device and first light source extending beyond an end of the insertion tube.

In a preferred embodiment, the endoscope assembly includes a locking mechanism that rotationally locks the insertion tube and imaging assembly.

In accordance with still yet another aspect of the invention, an endoscope assembly includes an insertion tube having a channel, an imaging assembly, and a locking mechanism. A portion of the imaging assembly is rotatably disposed inside the channel of the insertion tube, and the locking mechanism rotationally locks the insertion tube and imaging assembly.

In accordance with a further aspect of the invention, a major-minor endoscope includes a major endoscope having a first light source positioned proximate to one end and having a first imaging device positioned proximate to the one end, the major endoscope further including a channel along its length, a minor endoscope adapted for insertion into and through the channel of the major endoscope, the minor endoscope including an elongated body, a second light source positioned proximate to one end and having a second imaging device positioned proximate to the one end, a first polarizer positioned to polarize the light from the light source of one of the endoscopes, and a second polarizer positioned to polarize light received by the imaging device of the other endoscope. Preferably, the first polarizer is positioned to polarize the light from the light source of the major endoscope and the second polarizer is positioned to polarize the light received by the imaging device of the minor endoscope. Additionally, the first polarizer may be positioned to polarize the light from the light source of the minor endoscope and the second polarizer may be positioned to polarize the light received by the imaging device of the major endoscope. Furthermore, the first polarizer may be positioned to polarize the light from the light source of the major endoscope and the second polarizer may be positioned to polarize the light received by the imaging device of the minor endoscope. Preferably, the major-minor endoscope may further include a third polarizer positioned to polarize the light from the light source of the major endoscope and a fourth polarizer positioned to polarize the light received by the imaging device of the minor endoscope.

In accordance with a still further aspect of the invention, an endoscope includes an elongated body having a first imaging device positioned proximate to one end; and a first polarizer positioned to polarize light received by the imaging device.

In accordance with a yet further aspect of the invention, an endoscope and independently positionable polarized light source include the above endoscope and further include an independently positionable light source adapted for use within the human body. The light source may include an elongated body, a first light source proximate to one end, and a polarizer positioned to polarize the light emitted from the light source.

A yet still further aspect of the invention is directed to a pair of polarized endoscopes adapted for cooperative use within the human body. Each endoscope comprises an elongated body, an imaging device positioned proximate to one end, and a light source positioned proximate to the one end. A polarizer is positioned to polarize the light from the light source of one of the endoscopes and a second polarizer is positioned to polarize the light received by the imaging device of the other endoscope. The pair may further include a third polarizer positioned to polarize the light from the light source of the other endoscope and a fourth polarizer positioned to polarize the light received by the imaging device of the one endoscope.

DETAILED DESCRIPTION OF EMBODIMENTS OF THE INVENTION

Figure 1:
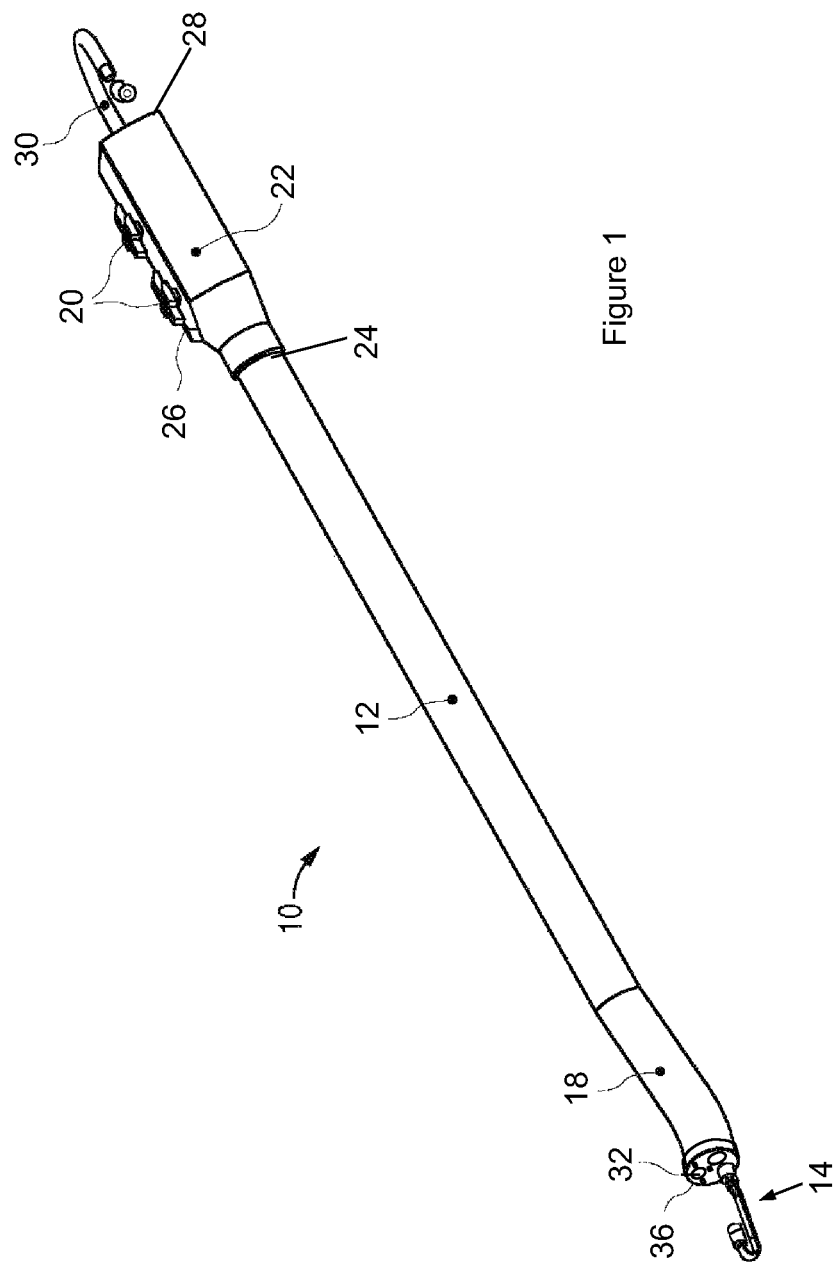
FIG. 1 shows a perspective view of an endoscope with an imaging assembly according to one embodiment of the present invention.

FIG. 1 illustrates a first exemplary endoscope 10 of the present invention. This endoscope 10 can be used in a variety of medical procedures in which imaging of a body tissue, organ, cavity or lumen is required. The types of procedures include, for example, anoscopy, arthroscopy, bronchoscopy, colonoscopy, cystoscopy, EGD, laparoscopy, and sigmoidoscopy.

Figure 2:
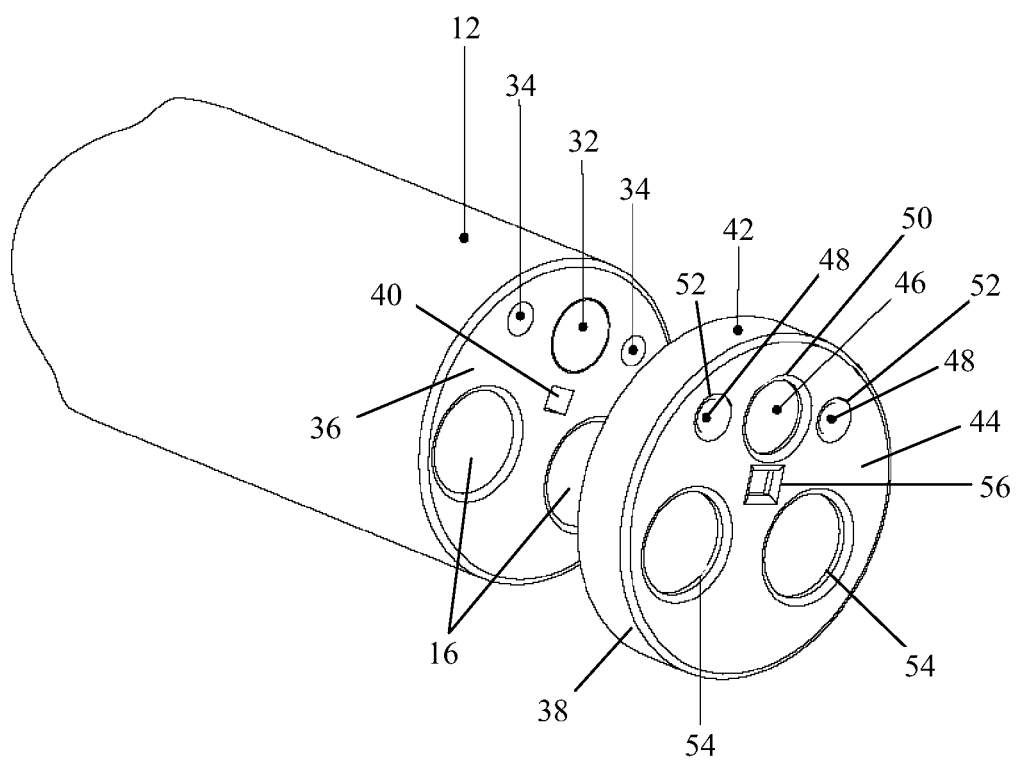
FIG. 2 shows a perspective view of the distal end of an insertion tube of the endoscope of FIG. 1 with a polarizer cap.

The endoscope 10 of FIG. 1 includes an insertion tube 12 and an imaging assembly 14, a section of which is housed inside the insertion tube 12. As shown in FIG. 2, the insertion tube 12 has two longitudinal channels 16. In general, however, the insertion tube 12 may have any number of longitudinal channels. An instrument can reach the body cavity to perform any desired procedures, such as to take samples of suspicious tissues or to perform other surgical procedures such as polypectomy. The instruments may be, for example, a retractable needle for drug injection, hydraulically actuated scissors, clamps, grasping tools, electrocoagulation systems, ultrasound transducers, electrical sensors, heating elements, laser mechanisms and other ablation means. In some embodiments, one of the channels can be used to supply a washing liquid such as water for washing. Another or the same channel may be used to supply a gas, such as $CO_2$ or air into the organ. The channels 16 may also be used to extract fluids or inject fluids, such as a drug in a liquid carrier, into the body. Various biopsy, drug delivery, and other diagnostic and therapeutic devices may also be inserted via the channels 16 to perform specific functions.

The insertion tube 12 preferably is steerable or has a steerable distal end region 18 as shown in FIG. 1. The length of the distal end region 18 may be any suitable fraction of the length of the insertion tube 12, such as one half, one third, one fourth, one sixth, one tenth, or one twentieth. The insertion tube 12 may have control cables (not shown) for the manipulation of the insertion tube 12. Preferably, the control cables are symmetrically positioned within the insertion tube 12 and extend along the length of the insertion tube 12. The control cables may be anchored at or near the distal end 36 of the insertion tube 12. Each of the control cables may be a Bowden cable, which includes a wire contained in a flexible overlying hollow tube. The wires of the Bowden cables are attached to controls 20 in the handle 22. Using the controls 20, the wires can be pulled to bend the distal end region 18 of the insertion tube 12 in a given direction. The Bowden cables can be used to articulate the distal end region 18 of the insertion tube 12 in different directions.

As shown in FIG. 1, the endoscope 10 may include a control handle 22 connected to the proximal end 24 of the insertion tube 12. Preferably, the control handle 22 has one or more ports and/or valves (not shown) for controlling access to the channels 16 of the insertion tube 12. The ports and/or valves can be air or water valves, suction valves, instrumentation ports, and suction/instrumentation ports. As shown in FIG. 1, the control handle 22 may additionally include buttons 26 for taking pictures with an imaging device on the insertion tube 12, the imaging assembly 14, or both.

The proximal end 28 of the control handle 22 may include an accessory outlet 30 (FIG. 1) that provides fluid communication between the air, water and suction channels and the pumps and related accessories. The same outlet 30 or a different outlet can be used for electrical lines to light and imaging components at the distal end of the endoscope 10.

Figure 5:
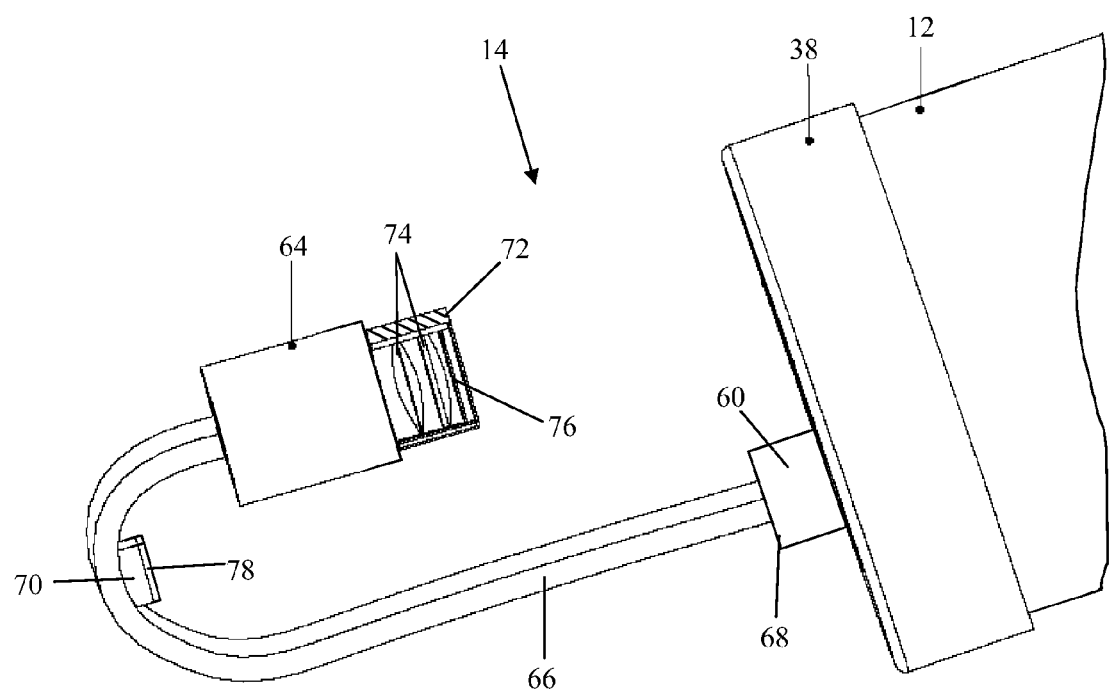
FIG. 5 shows a perspective view of the distal ends of the endoscope and imaging assembly of FIG. 1 with a cross-sectional view of the lens barrel of the imaging assembly.

As shown in FIG. 2, the endoscope 10 also includes a main imaging device 32 and main light sources 34, both of which are disposed at the distal end 36 of the insertion tube 12, and a polarizer cap 38 that is adapted to be mounted on the distal end 36 of the insertion tube 12 to cover the main imaging device 32 and main light sources 34. FIG. 2 shows the polarizer cap 38 removed from the distal end 36 of the insertion tube 12, and FIG. 5 shows the polarizer cap 38 mounted on the distal end 36 of the insertion tube 12.

The main imaging device 32 at the distal end 36 of the insertion tube 12 may include, for example, a lens, single chip sensor, multiple chip sensor or fiber optic implemented devices. The main imaging device 32, in electrical communication with a processor and/or monitor, may provide still images or recorded or live video images. The light sources 34 may be light emitting diodes (LEDs) or fiber optical delivery of light from an external light source. The light sources 34 preferably are equidistant from the main imaging device 32 to provide even illumination. The intensity of each light source 34 can be adjusted to achieve optimum imaging. The circuits for the main imaging device 32 and light sources 34 may be incorporated into a printed circuit board (PCB). As shown in FIG. 2, the insertion tube 12 has a channel 40 for supplying a liquid such as water for cleaning the lenses of the main imaging device 32 and the light sources 34.

Figure 3:
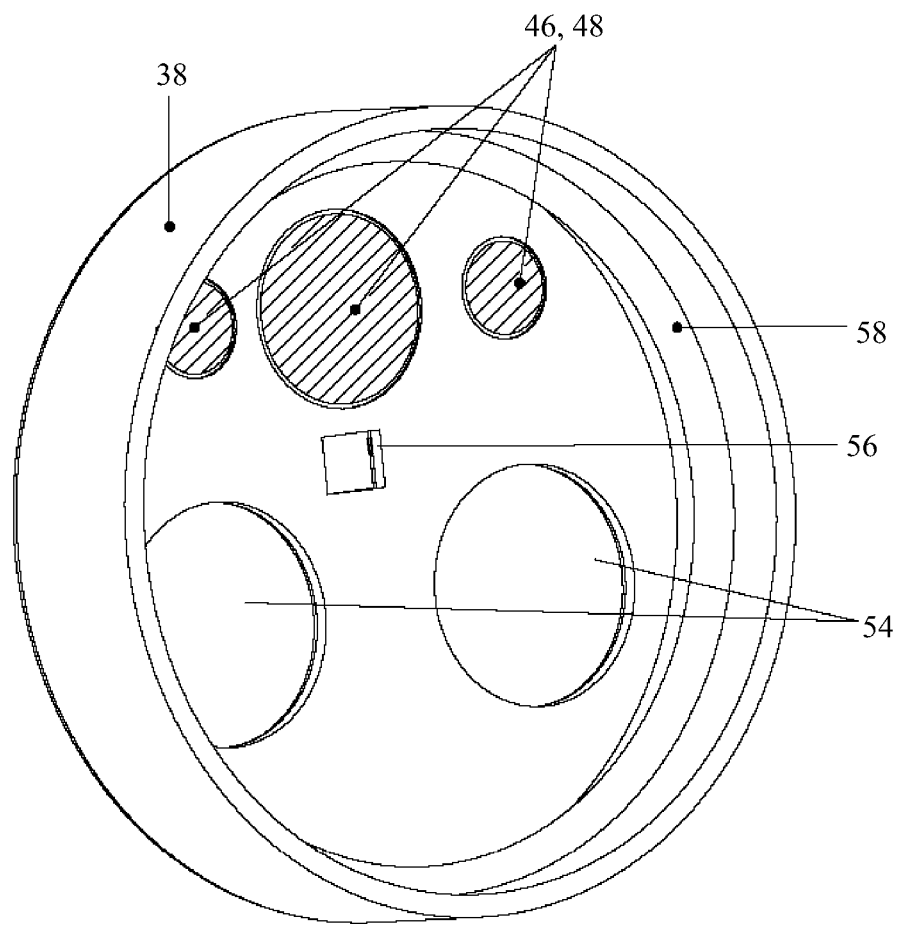
FIG. 3 shows a perspective back view of the polarizer cap of FIG. 2.

The polarizer cap 38, as shown in FIGS. 2 and 3, includes a cylindrical sidewall 42, an end wall 44, and polarizing filters 46, 48 mounted on the end wall 44. The cylindrical sidewall 42 and end wall 44 may form an integral part that is made by injection molding of a suitable biocompatible material such as medical grade plastics. The end wall 44 preferably has an opening 50 for accommodating the polarizing filter 46 for the main imaging device 32. The opening 50 may have any arrangement suitable for retaining the polarizing filter 46. For example, the opening 50 may have a recessed lip for receiving the polarizing filter 46. The polarizing filter 46 can be placed in the recessed lip and fixed there by adhesive bonding or by a mechanical snap fit.

The end wall 44 preferably has an opening 52 for accommodating the polarizing filter 48 for each of the light sources 34. The opening 52 may have any arrangement suitable for retaining the polarizing filter 48. One example of such suitable arrangement is the recessed lip described above. The end wall 44 preferably has an opening 54 for each of the instrument channels 16 so that the cap 38 does not block the channels 16.

The end wall 44 may further include an opening 56 for the channel 40 for supplying a liquid to clean the lenses of the imaging device 32 and the light sources 34. Preferably, the cap 38 has one or more features that allow liquid from the channel 40 to reach over the cap 38 to clean the exterior surfaces of polarizing filters 46, 48. For example, the end wall 44 of the cap 38 may be sufficiently thin to allow the liquid from the channel 40 to reach over the cap 38 to clean the exterior surfaces of polarizing filters 46, 48. Alternatively, the cap 38 may have variable thickness and/or angled features that allow liquid from the channel 40 to reach the polarizing filters 46, 48. Furthermore, the cap 38 may have a ramp, plate or channel that allows liquid from the channel 40 to reach the polarizing filters 46, 48. The locations, configurations and sizes of the openings 50, 52, 54, 56 preferably correspond to the locations, configurations and sizes of the main imaging device 32, light sources 34, channels 16, and clean liquid channel 40, respectively.

As shown in FIG. 3, the cap 38 preferably has a ring 58 located around the inner perimeter of the cap 38. The ring 58 helps secure the cap 38 to the distal end region of the insertion tube 12. In a preferred embodiment, the ring 58 is made from a compressive material such as silicon. Alternatively, the ring 58 can be made from other compressive materials, such as compressive rubbers, polymers and/or foams. The ring 58 may be attached the inner perimeter of the cap 38 by any suitable means such as adhesive bonding, mechanical over molding, or plastic snap features.

The inside diameter of the ring 58 preferably is slightly smaller than the outer diameter of the insertion tube 12 so that the ring 58 can apply a compressive force to the outer surface of the insertion tube 12. This compressive force preferably is sufficient to create the necessary friction force to ensure that the cap 38 remains in the same position and orientation during a medical procedure, yet to allow the cap 38 to be slide on and off of the insertion tube 12 without difficulty.

Alternatively, the cap 38 may have any other type of arrangement for attachment to the insertion tube 12. For example, the cap 38 may have clasps which snap on to the insertion tube 12. In some embodiments, the attachment may be similar to the way in which a suction cap for endoscopic mucosal resection is attached to a colonoscope, as is well known in the art.

The terms "polarizing filter" and "polarizer" as used in this specification refer to any device that blocks one or more components of light while allowing one or more other components to pass through. In some cases, polarizing filters may be made from a material that blocks light waves traveling in all planes from passing through the filter except for light waves propagating in one specific plane of orientation, often referred to as the plane of polarization or the plane of transmission. Polarizing filters may be constructed using various techniques that use light absorption, reflection, scattering or birefringence to block light from passing through the filter that is not orientated parallel with the plane of transmission.

When one polarizing filter is placed in front of another polarizing filter and non-coherent natural white light is passed through the two polarizing filters, the amount of light that passes through the two polarizing filters is proportional to the relative angle of orientation of the two filters. This is because when the polarization plane of the two filters is at the same angle of orientation, the majority of light waves in the plane of transmission will pass through both filters. As one of the filters is rotated, light that is polarized by the first filter is then attenuated or blocked by the second filter. The maximum amount of light reduction or extinction occurs when the polarizing planes of the two filters are orientated at 90° relative to each other. It is common to find polarizing filters that when orientated at 90° provide 99% or greater extinction of light transmission.

Figure 4:
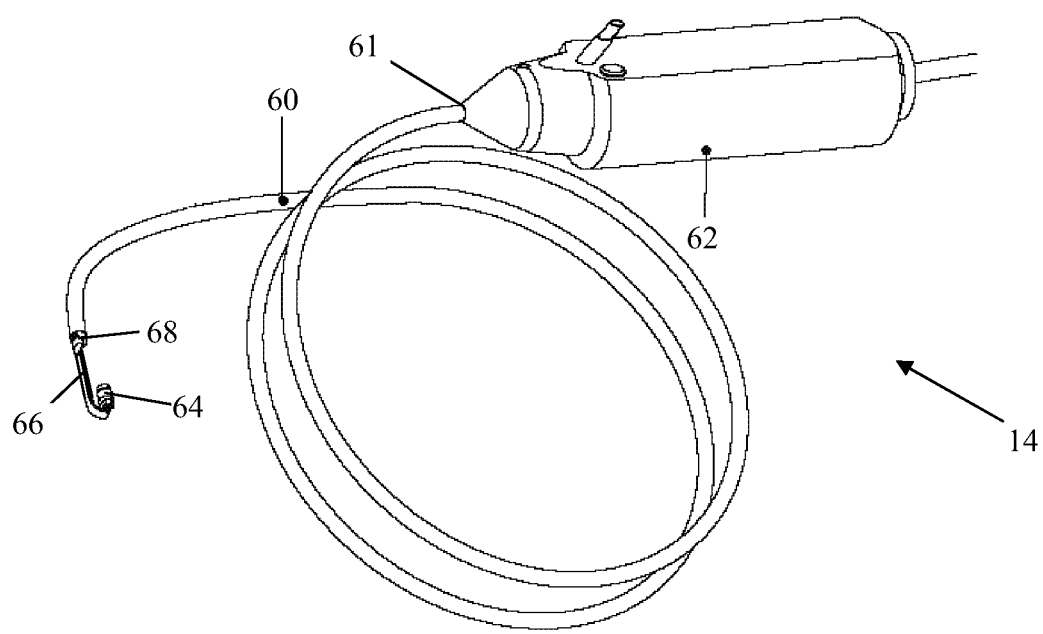
FIG. 4 shows a perspective view of the imaging assembly shown in FIG. 1.

As shown in FIGS. 4 and 5, the imaging assembly 14 may include a tubular body 60, a handle 62 connected to the proximal end 61 of the tubular body 60, an auxiliary imaging device 64, a link 66 that provides physical and/or electrical connection between the auxiliary imaging device 64 to the distal end 68 of the tubular body 60, and an auxiliary light source 70 (FIG. 5).

As shown in FIG. 5, the imaging assembly 14 is used to provide an auxiliary imaging device at the distal end of the endoscope 10. To this end, the imaging assembly 14 is placed inside one of the channels 16 of the endoscope's insertion tube 12 with its auxiliary imaging device 64 disposed beyond the distal end 36 of the insertion tube 12. This can be accomplished by first inserting the distal end of the imaging assembly 14 into the insertion tube's channel 16 from the endoscope's handle 18 and then pushing the imaging assembly 14 further into the assembly 14 until the auxiliary imaging device 64 and link 66 of the imaging assembly 14 are positioned outside the distal end 36 of the insertion tube 12 as shown in FIG. 5.

As shown in FIG. 5, the auxiliary imaging device 64 may include a lens barrel 72 having one or more lenses 74, an imaging sensor, and a printed circuit board (PCB). The imaging sensor may be an electronic device which converts light incident on photosensitive semiconductor elements into electrical signals. The imaging sensor may detect either color or black-and-white images. The signals from the imaging sensor can be digitized and used to reproduce an image that is incident on the imaging sensor. Two commonly used types of image sensors are Charge Coupled Devices (CCD) such as a VCC-5774 produced by Sanyo of Osaka, Japan and Complementary Metal Oxide Semiconductor (CMOS) camera chips such as an OVT 6910 produced by OmniVision of Sunnyvale, Calif.

The endoscope 10 preferably includes a polarizing filter 76 placed in front of the auxiliary imaging device 64. The polarizing filter 76 may be placed inside the lens barrel 72. Alternatively, the polarizing filter 76 may be placed directly onto the image sensor itself, or incorporated at various other locations in the lens barrel 72 such as at the end closest to the imaging sensor, or even between the lenses 74. Furthermore, the polarizing filter 76 may be simply placed in front of the auxiliary imaging device.

When the imaging assembly 14 is properly installed in the insertion tube 12, the auxiliary imaging device 64 of the imaging assembly 14 preferably faces backwards towards the main imaging device 32 as illustrated in FIG. 3. The auxiliary imaging device 64 may be oriented so that the auxiliary imaging device 64 and the main imaging device 32 have adjacent or overlapping viewing areas. Alternatively, the auxiliary imaging device 64 may be oriented so that the auxiliary imaging device 64 and the main imaging device 32 simultaneously provide different views of the same area. Preferably, the auxiliary imaging device 64 provides a retrograde view of the area, while the main imaging device 32 provides a front view of the area. However, the auxiliary imaging device 64 could be oriented in other directions to provide other views, including views that are substantially parallel to the axis of the main imaging device 32.

As shown in FIGS. 2 and 3, the link 66 connects the auxiliary imaging device 64 to the distal end 68 of the tubular body 60. Preferably, the link 66 is a flexible link that is at least partially made from a flexible shape memory material that substantially tends to return to its original shape after deformation. Shape memory materials are well known and include shape memory alloys and shape memory polymers. A suitable flexible shape memory material is a shape memory alloy such as nitinol. The flexible link 66 is straightened to allow the distal end of the imaging assembly 14 to be inserted into the proximal end of assembly 14 of the insertion tube 12 and then pushed towards the distal end 36 of the insertion tube 12. When the auxiliary imaging device 64 and flexible link 66 are pushed sufficiently out of the distal end 36 of the insertion tube 12, the flexible link 66 resumes its natural bent configuration as shown in FIG. 3. The natural configuration of the flexible link 66 is the configuration of the flexible link 66 when the flexible link 66 is not subject to any force or stress. When the flexible link 66 resumes its natural bent configuration, the auxiliary imaging device 64 faces substantially back towards the distal end 36 of the insertion tube 12 as shown in FIG. 5.

In the illustrated embodiment, the auxiliary light source 70 (as well as other components) of the imaging assembly 14 is placed on the flexible link 66, in particular on the curved concave portion of the flexible link 66. The auxiliary light source 70 provides illumination for the auxiliary imaging device 64 and may face substantially the same direction as the auxiliary imaging device 64 as shown in FIG. 5.

The endoscope 10 includes another polarizing filter 78 placed in front of the auxiliary light source 70. The polarizing filter 78 may be attached to the auxiliary light source 70 by any suitable means such as adhesive bonding or welding.

The flexible link 66 may be encapsulated or shrouded by flexible tubing, heat-shrinkable tubing, urethanes, rubber or silicon so as to allow smooth profile transition from the tubular body 60 to the imaging device 64. This encapsulation may be translucent to allow light from the light source 70 to project through the encapsulation, or the encapsulation may include a window section around the light source 70.

Since the main imaging device 32 and its light source 34 face the auxiliary imaging device 64 and its light source 70, the light sources 34, 45 of the imaging devices 32, 64 may interfere with the opposing imaging device 64, 32. That is, the main light source 34 may shine directly into auxiliary imaging device 64 and the auxiliary light source 70 may shine directly into the main imaging device 32, degrading both images.

To eliminate or reduce the light interference, the polarization plane of the polarizing filter 46 for the main imaging device 32 may be set at a substantially 90° angle from the polarization plane of the polarizing filter 78 for the auxiliary light source 70. With this arrangement, the light, which is emitted from the auxiliary light source 70 and passes though the polarizing filter 78, may be filtered out by the polarizing filter 46 and may not reach the main imaging device 32.

Additionally or alternatively, the polarization plane of the polarizing filter 76 for the auxiliary imaging device 64 may be set at a substantially 90° angle from the polarization plane of the polarizing filters 48 for the main light sources 34. With this arrangement, the light, which is emitted from the main light sources 34 and passes though the polarizing filters 48, may be filtered out by the polarizing filter 76 and may not reach the auxiliary imaging device 64.

Moreover, to provide illumination, the polarization plane of the polarizing filter 46 for the main imaging device 32 may be substantially aligned with the polarization plane of the polarizing filters 48 for the main light sources 34 so that the light, which is emitted from the main light sources 34 and passes though the polarizing filters 48, may pass through the polarizing filter 46 and may be received by the main imaging device 32. Additionally or alternatively, the polarization plane of the polarizing filter 76 for the auxiliary imaging device 64 may be substantially aligned with the polarization plane of the polarizing filter 78 for the auxiliary light source 70 so that the light, which is emitted from the auxiliary light source 70 and passes though the polarizing filter 78, may pass through the polarizing filter 76 and may be received by the auxiliary imaging device 64.

The desired relative orientations of the polarizing filters' the polarization planes, as set forth above, may be achieved in any suitable manner. For example, the polarization planes of the polarizing filters 46, 48 for the main imaging device 32 and main light sources 34 may be aligned and fixed in the polarizer cap 38, and the polarization planes of the polarizing filters 76, 78 for the auxiliary imaging device 64 and auxiliary light source 70 may be aligned and fixed in the imaging assembly 14. Then the imaging assembly 14 may be rotated within the channel 16 of the insertion tube 12 by means of its handle 62 until the polarization planes of the polarizing filters 76, 78 in the imaging assembly 14 are at a substantially 90° angle from the polarization planes of the polarizing filters 46, 48 in the polarizer cap 38.

The orientations of the polarizing filters' the polarization planes may be determined and set during attachment by viewing a light with a known polarization passing through polarizing filters. Alternatively, the polarizing filters may have asymmetrical shapes or other locating features so that the orientations of their polarization planes may be readily determined.

The auxiliary imaging device 64 and its light source 70 may be connected to a control box (not shown) via electrical conductors that extend from the imaging device 64 and light source 70; through the link 66, tubular body 60, and handle 62; to the control box. The electrical conductors may carry power and control commands to the auxiliary imaging device 64 and its light source 70 and image signals from the auxiliary imaging device 64 to the control box.

The control box includes at least an image and signal processing device and a housing in which the image and signal processing device is disposed, although the control box can be configured in any suitable manner. The housing may include a control panel and connectors. The control panel includes buttons and knobs for controlling the functionalities of the control box.

The image and signal processing device may include one or more integrated circuits and memory devices along with associated discrete components. The device allows image signals from the imaging devices 32, 64 to be processed for the enhancement of image quality, extraction of still images from the image signals, and conversion of video format for compatibility with the display device.

The control box preferably processes the video image signal from the auxiliary imaging device 64 and transmits it to a display device such as a television or a monitor such as a liquid crystal display monitor. Still images can be captured from the video image signal. The video image or still image may be displayed on the display device. The display device may also include textual data that are used to display information such as patient information, reference numbers, date, and/or time.

The image signal from the main imaging device 32 may also be processed by the control box in the same way that the image signal from the auxiliary imaging device 64 is processed. The images from the main and auxiliary imaging devices 32, 64 may be displayed on two separate monitors or on the same monitor with a split screen.

The control box may further be used to adjust the parameters of the imaging devices 32, 64 and their light sources 34, 70, such as brightness, exposure time and mode settings. The adjustment can be done by writing digital commands to specific registers controlling the parameters. The registers can be addressed by their unique addresses, and digital commands can be read from and written to the registers to change the various parameters. The control box can change the register values by transmitting data commands to the registers.

The control box may additionally be used as an interface to the patient records database. A large number of medical facilities now make use of electronic medical records. During the procedure relevant video and image data may need to be recorded in the patient electronic medical records (EMR) file. The signal processing circuit can convert image and video data to a format suitable for filing in the patient EMR file such as images in .jpeg, tif, or .bmp format among others. The processed signal can be transmitted to the medical professional's computer or the medical facilities server via a cable or dedicated wireless link. A switch on the control panel can be used to enable this transmission. Alternatively the data can be stored with a unique identification for the patient in electronic memory provided in the control box itself. The signal processing circuit can be utilized to convert the video and image data to be compatible with the electronic medical records system used by the medical professional. The processing may include compression of the data. A cable or a wireless link may be used to transmit the data to a computer.

During endoscopy, a technician may first install the polarizer cap 38 onto the endoscope's insertion tube 12. A physician may then insert the endoscope into a body cavity through an orifice of the body. Once the endoscope is inserted, the physician may decide to use the imaging assembly 14 in order to obtain a rear-viewing image of a certain tissue. The physician may straighten the flexible link 66 of the imaging assembly 14 and insert the straightened distal end of the imaging assembly 14 into the channel 16 of the endoscope's insertion tube 12 from the handle 22. The imaging assembly 14 can then be pushed towards the distal end 36 of the insertion tube 12. When the auxiliary imaging device 64 and flexible link 66 are pushed out of the distal end 36 of the insertion tube 12, the flexible link 66 resumes its natural bent configuration as shown in FIG. 2. The main imaging device 32 now captures a front-viewing image, and the auxiliary imaging device 64 simultaneously captures a rear-viewing image of the same area. The physician may then rotate the imaging assembly 14 so that the polarization planes of the polarizing filters 76, 78 in the imaging assembly 14 are at a substantially 90° angle from the polarization planes of the polarizing filters 46, 48 in the polarizer cap 38. Once the correct orientation has been established, the physician locks or fixes the orientation of the imaging assembly 14 relative to the insertion tube 12. The physician then continues with the procedure.

The above-described embodiment is merely one of many alternative embodiments of the present invention. In one other alternate embodiment, polarizing filters are placed over only the auxiliary imaging device 64 of the imaging assembly 14 and the main light sources 34 to reduce light interference between them. In this embodiment, a low intensity auxiliary light source 70 may be used for the auxiliary imaging device 64 to alleviate any bright spots that could be seen by the main imaging device 32. This arrangement allows maximum light intake by the main imaging device 32 without light loss caused by a polarizing filter. Similarly, in another alternative embodiment, polarizing filters are placed over only the main imaging device 32 and the auxiliary imaging device 64. These two embodiments are useful depending on the types of imaging sensors used in the endoscope, specifically their light sensitivities, resistance to blooming, and dynamic ranges, as well as depending on the types of light sources used in the endoscope and their illumination intensities and/or wave length spectrums.

In another alternate embodiment, the main imaging device 32 and main light sources 34 may share a polarizing filter. For example, the polarizer cap mounted on the distal end of the insertion tube may have a large polarizing filter approximately the size of the cap's end wall. This large filter may have openings for the channels 16 of the insertion tube 12. Alternatively, the filter may occupy only the area of the cap's end wall in front of the main imaging device 32 and main light sources 34. This embodiment allows for the orientation of the polarization plane in front of the main imaging device 32 and main light sources 34 to be precisely orientated.

In general, a polarizing filter may be placed in a cap mounted in front of an imaging device, placed in the lens assembly of the imaging device, or attached to the front of the imaging device. Various techniques for attachment may be used, such as ring and clamp arrangements, snap fit or plastic friction fit arrangements, or even permanent bonding. Alternatively, polarizing filters may be placed along the optical path of the fiber optic bundles that run along the length of the endoscope, or even placed in an external light source box.

In still another alternate embodiment, a cap with one or more polarizing filters, similar to the cap 38 shown in FIGS. 2 and 3, may be placed on the auxiliary imaging device 64.

Figure 6:
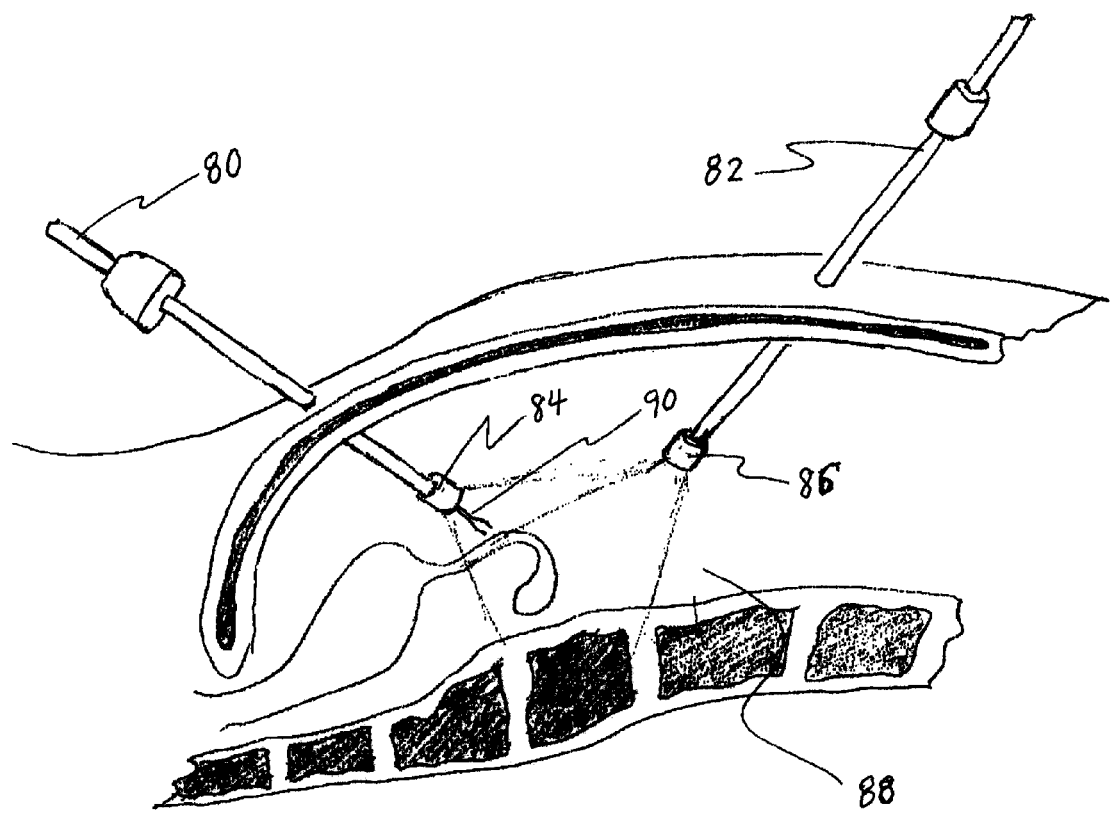
FIG. 6 shows a cross-sectional view of a peritoneal cavity with multiple endoscopes.

In yet another alternate embodiment, as shown in FIG. 6, when multiple endoscopes 80, 82, which may be considered as an endoscope assembly, are used during a procedure, such as during laparoscopy or arthroscopy, a polarizer cap 84, 86 may be placed over one or more of the endoscopes 80, 82 to reduce light interference caused by endoscopes 80, 82. In FIG. 6, the endoscopes 80, 82 are inserted into a peritoneal cavity 88. Preferably, at least one of the endoscopes 80, 82 has a channel that allows a surgical tool 90 to access the peritoneal cavity 88. In the illustrated embodiment, one or more of the endoscopes 80, 82 may have a light source. In some cases, each and every one of the endoscopes 80, 82 has a light source. Similarly, one or more of the endoscopes 80, 82 may have an imaging device. In some cases, each and every one of the endoscopes 80, 82 has an imaging device. In one particular case, only one of the endoscopes has a light source, while each of the other endoscopes has only an imaging device. In the illustrated embodiment, the polarizing filters of the same cap 84, 86 may have the same plane of polarization, and the polarizing filters of the different caps 84, 86 may have different planes of polarization. Alternatively, the caps may have the same plane of polarization but a physician can rotate one or more endoscopes to the appropriate orientations. If only two endoscopes 80, 82 are used, the two caps 84, 86 may have their planes of polarization orientated at 90° from one another. If only three endoscopes are used, the three caps may have polarization planes orientated at 120° relative to one another so as to provide a significant cancellation of light interference at each endoscope.

In a further alternate embodiment, the endoscope may have orientation arrangements on both the polarizer cap and the imaging assembly such that the orientation between polarizing filters may be easily adjusted. One such embodiment includes a small magnet that is permanently fixed to the polarizer cap, and a metallic element fixed to the imaging assembly. The magnet may be a rare earth magnet such as a Neodymium Iron Boron type permanent magnet. The orientation of the magnet and metallic element is designed such that the magnetic field generated by the magnet will attract the metallic element most strongly when the polarizing filters are properly aligned. In this manner, when the metallic element is in close proximity to the magnet, it will naturally be pulled by the magnet into the correct position. Furthermore, when the magnet and metallic element come into contact, an attachment is formed which resists change of orientation and maintains the proper orientation between the polarizing filters. Only when a substantial force is applied, such as when the physician forcefully advancing the imaging assembly, will the magnetic attachment be broken, allowing the physician to re-align or remove the imaging assembly. Alternatively, the magnet may be placed in the imaging assembly and a metallic element may be located on the cap. Furthermore, magnets may be used on both the imaging assembly and the cap.

In still a further alternate embodiment, the orientation features include a feature, such as a pin, rod or geometric feature, affixed to and protruding slightly away from the imaging assembly, and a feature, such as a cup and tube, on the polarizer cap that mates with the corresponding feature on the imaging assembly. The features may be made from a compressive material such as rubber so that when the two features are engaged a substantial force is needed to break the engagement. In this manner, the physician would first slide the imaging assembly past the distal end of the insertion tube and then, under the guidance of the auxiliary imaging device, rotate the imaging assembly to achieve the correct relative orientation between the polarizing filters. When the correct relative orientation between the polarizing filters is achieved, the physician may retract the imaging assembly so that the two features engage and lock together. To later disengage the features, the physician may forcefully advance the imaging assembly.

In yet a further alternate embodiment, the distal end of the imaging assembly includes a mechanism that can fix the position of the imaging assembly in the channel of the insertion tube. Such a mechanism may include the use of inflatable balloons, springs that are actuated via guide-wires, mechanical engagement arrangements, or frictional methods such as large diameter compressive regions incorporating rubber or foam.

In the present application, the terms "insertion tube," "imaging assembly" and "endoscope" are interchangeable, may have the same or similar meanings, and may have the same or similar features and functions. Different terms are used in the application for ease of identification and description. Additionally, such a description should not be used to limit the breadth of the application. The use of "insertion tube," "imaging assembly", or "endoscope" merely refers to possible types of instruments in the broad field of endoscopy and the invention may be applied to many forms of endoscopes and medical imaging devices.

Furthermore, the configuration of one endoscope that is inserted through the channel of another endoscope (such as the imaging catheter being inserted through the main endoscope as described in the preferred embodiments) can be referred to as a major-minor endoscope configuration, where the larger diameter endoscope is referred to as the major endoscope and the smaller diameter endoscope as the minor endoscope.

The invention claimed is:

1. An endoscope assembly, comprising:
    an endoscope comprising a first image sensor, a first light source, and a first polarizing filter, wherein the first polarizing filter is disposed over the first light source; and
    an imaging device comprising a second image sensor, a second light source, a second polarizing filter, wherein the second polarizing filter is disposed over the second image sensor, and a curved link configured to extend from a distal end of the endoscope such that the second image sensor and second light source face the first image sensor and first light source, wherein the first and second polarizing filters are configured to reduce light interference between the first light source and the second image sensor, wherein the second polarizing filter blocks light that is transmitted through the first polarizing filter, and wherein there is no polarizing filter over the first image sensor and no polarizing filter over the second light source.

2. The endoscope assembly of claim 1, wherein the curved link comprises a shape-memory material.

3. The endoscope assembly of claim 1, further comprising a cap, wherein the first polarizing filter is disposed on the cap.

4. The endoscope assembly of claim 3, wherein the first image sensor and the first light source are located at a distal portion of the endoscope, and wherein the cap is mounted on the distal end of the endoscope.

5. The endoscope assembly of claim 1, wherein the imaging device further comprises a lens assembly, and wherein the second polarizing filter is disposed in the lens assembly.

6. The endoscope assembly of claim 1, wherein the first polarizing filter has a first plane of polarization and the second polarizing filter has a second plane of polarization, wherein the first plane of polarization of the first polarizing filter is at a substantially 90° angle from the second plane of polarization of the second polarizing filter.

7. The endoscope assembly of claim 1, further comprising a cap, wherein the second polarizing filter is disposed on the cap.

8. The endoscope assembly of claim 7, wherein the cap is mounted on a distal end of the curved link.

9. The endo scope assembly of claim 1, wherein the first light source is positioned to illuminate a field of view of the first image sensor, and wherein the second light source is positioned to illuminate a field of view of the second image sensor.

10. The endoscope assembly of claim 1, wherein the endoscope has a channel, wherein a portion of the imaging device is rotatably disposed inside the channel of the endoscope, and wherein the second image sensor and the second light source extend beyond an end of the endoscope channel.

11. The endoscope assembly of claim 10, further comprising a locking mechanism that rotationally locks the position of the imaging device with respect to the endoscope.

12. The endoscope assembly of claim 1, wherein the endoscope has a channel, wherein a portion of the imaging device is slidably disposed inside the channel of the endoscope, and wherein the second image sensor and the second light source extend beyond an end of the endoscope channel.

13. A major-minor endoscope comprising:
    a major endoscope having a first light source and a first image sensor located at a distal end of the major endoscope, the major endoscope further including a channel along its length;
    a minor endoscope adapted for insertion into and through the channel of the major endoscope, the minor endoscope including an elongated body with a curved distal portion, a second light source, and a second image sensor located at the distal end of the elongated body, wherein the second image sensor and second light source face the first image sensor and the first light source when the distal end of the minor endoscope exits the channel of the major endoscope;
    a first polarizing filter disposed over the first light source; and
    a second polarizing filter disposed over the second image sensor, wherein the first and second polarizing filters are configured to reduce light interference between the first light source and the second image sensor, wherein the second polarizing filter is configured to block light that is transmitted through the first polarizing filter, and wherein there is no polarizing filter disposed over the first image sensor and there is no polarizing filter over the second light source.

14. A pair of endoscopes adapted for cooperative use within the human body, comprising:
    a first endoscope comprising a first image sensor, a first light source, and a first polarizing filter, wherein the first polarizing filter is disposed over the first light source;
    a second endoscope comprising a second image sensor, a second light source, and a second polarizing filter, wherein the second polarizing filter is disposed over the second image sensor, wherein the first and second polarizing filters are configured to reduce light interference between the first light source and the second image sensor, wherein the second polarizing filter blocks light that is transmitted through the first polarizing filter, and wherein there is no polarizing filter disposed over the first image sensor and there is no polarizing filter over the second light source.

* * * * *